US011951093B2

(12) United States Patent
Bodor

(10) Patent No.: US 11,951,093 B2
(45) Date of Patent: Apr. 9, 2024

(54) METHODS AND COMPOSITIONS FOR SOFT ANTICHOLINERGIC ESTERS

(71) Applicant: Bodor Laboratories, Inc., Miami, FL (US)

(72) Inventor: Nicholas S. Bodor, Bal Harbour, FL (US)

(73) Assignee: BODOR LABORATORIES, INC., Miami, FL (US)

( * ) Notice: Subject to any disclaimer, the term of this patent is extended or adjusted under 35 U.S.C. 154(b) by 0 days.

(21) Appl. No.: 17/848,386

(22) Filed: Jun. 23, 2022

(65) Prior Publication Data
US 2022/0401410 A1    Dec. 22, 2022

Related U.S. Application Data

(62) Division of application No. 15/758,190, filed as application No. PCT/US2016/050385 on Sep. 6, 2016, now Pat. No. 11,534,422.

(60) Provisional application No. 62/217,362, filed on Sep. 11, 2015.

(51) Int. Cl.
| | |
|---|---|
| *A61K 31/40* | (2006.01) |
| *A61K 9/00* | (2006.01) |
| *A61K 9/20* | (2006.01) |
| *A61K 9/70* | (2006.01) |
| *A61K 47/38* | (2006.01) |
| *A61K 47/40* | (2006.01) |
| *A61P 1/02* | (2006.01) |
| *C07D 207/10* | (2006.01) |
| *C07D 207/12* | (2006.01) |

(52) U.S. Cl.
CPC ............ *A61K 31/40* (2013.01); *A61K 9/0056* (2013.01); *A61K 9/006* (2013.01); *A61K 9/2054* (2013.01); *A61K 9/7007* (2013.01); *A61K 47/38* (2013.01); *A61K 47/40* (2013.01); *A61P 1/02* (2018.01); *C07D 207/10* (2013.01); *C07D 207/12* (2013.01)

(58) Field of Classification Search
CPC ...... A61K 31/40; A61K 9/0056; A61K 9/006; A61K 9/2054; A61K 9/7007; A61K 47/38; A61K 47/40; A61P 1/02; A61P 25/00; C07D 207/10; C07D 207/12
See application file for complete search history.

(56) References Cited

U.S. PATENT DOCUMENTS

| | | | |
|---|---|---|---|
| 6,495,120 B2 | 12/2002 | McCoy | |
| 7,399,861 B2 | 7/2008 | Bodor | |
| 7,417,147 B2 | 8/2008 | Bodor | |
| 7,538,219 B2 | 5/2009 | Bodor | |
| 7,576,210 B2 | 8/2009 | Bodor | |
| 8,071,639 B2 | 12/2011 | Bodor | |
| 8,071,693 B2 | 12/2011 | Banerjee et al. | |
| 8,147,809 B2 | 4/2012 | Bodor | |
| 8,568,699 B2 | 10/2013 | Bodor | |
| 8,628,729 B2 | 1/2014 | Bodor | |
| 8,628,759 B2 | 1/2014 | Bodor | |
| 9,198,897 B2 | 12/2015 | Merello et al. | |
| 9,220,707 B2 | 12/2015 | Bodor et al. | |
| 2002/0055496 A1 | 5/2002 | McCoy et al. | |
| 2008/0102102 A1 | 5/2008 | Merello et al. | |
| 2008/0260823 A1 | 10/2008 | Dillaha | |
| 2008/0317832 A1 | 12/2008 | Dillaha | |
| 2012/0141401 A1 | 6/2012 | Bodor | |
| 2012/0177590 A1 | 7/2012 | Bodor | |
| 2014/0275204 A1 | 9/2014 | Bodor et al. | |

FOREIGN PATENT DOCUMENTS

WO    2001/08681 A1    2/2001

OTHER PUBLICATIONS

International Search Report and Written Opinion of the International Searching Authority dated Nov. 29, 2016, Issued in corresponding International Application No. PCT/US2016/50385, 10 pages.
Hockstein, Neil G. et al., "Sialorrhea: A Management Challenge", American Academy of Family Physicians, vol. 69, pp. 2628-2634, American Academy of Family Physicians (2004).
NH004—Treatment of Sialorrhea, NeuroHealing Pharmaceuticals Inc., NH004 program Summary, 2015, 3 pages.
Mier, Richard J. et al., "Treatment of Sialorrhea With Glycopyrrolate: A Double-blind, Dose-Ranging Study", Arch Pediatr Adolesc Med., vol. 154, pp. 1214-1218, American Medical Association, (2000).
Zeller, Robert S. et al., "Randomized Phase III evaluation of the efficacy and safety of a novel glycopyrrolate oral solution for the management of chronic severe drooling in children with cerebral palsy or other neurologic conditions", Therapeutics and Clinical Risk Management, vol. 8, pp. 15-23, Dove Medical Press Ltd. (2012).

(Continued)

*Primary Examiner* — Savitha M Rao
*Assistant Examiner* — Andrew P Lee
(74) *Attorney, Agent, or Firm* — SHEPPARD, MULLIN, RICHTER & HAMPTON LLP

(57) ABSTRACT

Intra-oral formulations comprising soft anticholinergic alkyl esters are useful for treating excessive drooling conditions in subjects, such as humans, suffering from sialorrhea. Preferably, at least one soft anticholinergic ester is provided in an effective amount or concentration in an anhydrous intra-oral formulation that can inhibit excessive drooling resulting from a condition known as sialorrhea.

58 Claims, No Drawings

(56) References Cited

OTHER PUBLICATIONS

Ji. F., et al., "Synthesis and Pharmacological Effects of New N-Substituted Soft Anticholinergics Based on Glycopyrrolate," J. Pharmacy and Pharmacology, vol. 57, No. 11, Nov. 1, 2005, pp. 1427-1435, John Wiley & Sons LTD. London, GB (pub.).
Japanese Office Action dated Jun. 30, 2020 in corresponding Japanese Patent Application No. 2018-513004 and [!] English translation, 7 pages.
H. Takafumi, "Hypersalivation Induced by Olanzapine with Fluvoxamine", Progress in Neuro-Psychopharmacology and Biological Psychiatry, (2006), 30 EPNPBP 4, pp. 758-760.
R. Jackson, Wine Tasting a Professional Handbook, Second Edition, (2009), p. 448.
P. Jongerius et al., "A Systematic Review for Evidence of Efficacy of Anticholinergic Drugs to Treat Drooling", Arch Dis Child (2003), 88 pp. 911-914.
Loxitane (Loxapine Succinate USP Capsules, Loxitane c (Loxapine Hydrochloride) Oral Concentrate, Loxitane IM (Loxapine Hydrochloride) for Intramuscular Use Only, pp. 1-9.
Paxil (paroxetine hydrochloride) Tablets and Oral Suspension, pp. 1-49.
Chlorpromazine Hydrochloride Tablets, USP, 10 mg, 25 mg, 50 mg, 100 mg, and 200 mg (Nov. 2020) pp. 1-17.
R. Jackson, "Wine, Food, and Health", Elsevier, Wine Science, Chapter 12, (Apr. 2020) pp. 947-978.
Yokozeki, "A phase 3, multicenter, randomized, double-blind, vehicle-controlled, parallel-group study of 5% sofpironium bromide (BBI-4000) gel in Japanese patients with primary axillary hyperhidrosis", Journal of Dermatology 2021;48:279---288.
Brickell Bio, Sofpironium Bromide U.S. Phase 3 Pivotal Program Topline Results, Making Fresh Tracks® in Medicine, Oct. 7, 2021.
Wu et al., "Stereoisomers of N-substituted soft anticholinergics and their zwitterionic metabolite based on blycopyrrolate -syntheses and pharmacological evaluations", Pharmazie 63: 200-2019 (2008).
Patocka et al., "Acetylcholinesterase and Butyrylcholinesterase—Important Enzymes of Human Body", Acta Medica (Hradee Kralove) 47(4):215-228 (2004).
Lockridge, "Review of human butyrylcholinesterase structure, function, genetic variants, history of use in the clinic, and potential therapeutic uses", Pharmacoloty & Therapeutics 148; 34-36 (2015).
Evatt, "Oral glycopyrrolate for the treatment of chronic severe drooling caused bt neurological disorders in children", Neuropsychiatric Disease and Treatment, 7 543-547 (2011).
Written Opinion of the Intellectual Property Office of Singapore (IPOS), Apr. 15, 2019, Singapore Application No. 11201801996P, based on Internationa! Application No. PCT/US20'16/050385.
Stenzaly-Achtert, S. et al., "Axillary pH and Influence of deodorants", Skin Research and Technology 2000; 6: pp. 87-89.
Baliga, S. et al., Salivary pH: A Diagnostic Biomarker, J Indian Society Periodontal. Jul.-Aug. 2003: 17(4): pp. 461-465.
Samir, S. et al., "Identification of Major Esterase Involved in Hydrolysis of Soft Anticholinergic (2R3'R-SGM) Desinged from Glycopyrrolate in Human and Rat Tissues", Journal of Pharmaceutical Sciences, 108 {2019} pp. 2791-2797.
Singh, Simranjit et al., Evaluation of Serum and Salivary Lipid Profile: A Correlative Study. Journal of Oral and Maxillofacial Pathology, vol. 18, Issue 1 Jan.-Apr. 2014 pp. 4-8.
Mackness, Bharti, et al., "Human Tissue Distribution of Paraoxonases 1 and 2 mRNA", Life, 62 (6): p. 480-482, Jun. 2010.
European Search Report, European Patent Office, dated Apr. 9, 2019, Application No. 16844930.4-1114.13347007, based on International Application No. PCT/ US2016/050385.

METHODS AND COMPOSITIONS FOR SOFT ANTICHOLINERGIC ESTERS

CROSS REFERENCE TO RELATED APPLICATIONS

This application is a divisional of U.S. patent application Ser. No. 15/758,190, filed Mar. 7, 2018, which is the U.S. National Stage of International Patent Application No. PCT/US2016/050385, filed Sep. 6, 2016, which claims benefit from U.S. Provisional Patent Application No. 62/217,362, filed Sep. 11, 2015, all hereby expressly incorporated by reference in their entireties and relied upon and assigned to the assignee hereof.

BACKGROUND

Various anticholinergic compounds and formulations for those compounds have been previously described. Muscarinic receptor antagonists are frequently used therapeutic agents that inhibit the effects of acetylcholine by blocking its binding to muscarinic cholinergic receptors at neuroeffector sites on smooth muscle, cardiac muscle, and gland cells as well as in peripheral ganglia and in the central nervous system (CNS). However, their side effects, which can include dry mouth, photophobia, blurred vision, urinary hesitancy and retention, drowsiness, dizziness, restlessness, irritability, disorientation, hallucinations, tachycardia and cardiac arrhythmias, nausea, constipation, and severe allergic reactions, often limit their clinical use. Local administration of anticholinergic agents to targeted areas, such as the oral mucosa, where the localized blockage of muscarinic receptors will be of clinical benefit, would be a desirable therapeutic strategy. However, currently used locally active anticholinergics can exhibit unwanted systemic side effects which can limit the dosage that can be safely administered.

Glycopyrrolate is among the quaternary ammonium anticholinergics which have reduced CNS-related side effects as they cannot cross the blood-brain barrier; however, because glycopyrrolate is eliminated mainly as unchanged drug or active metabolite, its topical and other local administration is often associated with common undesirable anticholinergic systemic side effects. To increase the therapeutic index of anticholinergics, the soft drug approach has been applied in a number of different designs starting from various lead compounds, but there is a need for yet other new soft anticholinergics with clinically meaningful biological activity. These novel muscarinic antagonists, just as all other soft drugs, are designed to elicit their intended pharmacological effect at the site of application, but to be quickly metabolized into their designed-in, inactive metabolite upon entering the systemic circulation and to be rapidly eliminated from the body, resulting in reduced systemic side effects and an increased therapeutic index.

Soft anticholinergic zwitterions have been described in U.S. Patent Publication No. 2012/0141401 (now U.S. Pat. No. 8,568,699), and its related patents, U.S. Pat. Nos. 8,071,639; 7,538,219; and 7,417,147. Soft anticholinergic esters have been described in US Patent Publication No. 2012/0177590 (now U.S. Pat. No. 8,628,759) and its related patents U.S. Pat. Nos. 8,147,809; 7,576,210; and 7,399,861. Although these published applications and patents identified the potential for the zwitterion or ester forms of anticholinergics to be used for treating various conditions, the fact that activity and duration of action against sialorrhea are unexpectedly high herein, based on a comparison to published mydriasis data, was not known or previously described. Indeed, treatment of sialorrhea with these particular compounds was not previously suggested.

Each of the US Patent Publication Nos. 2012/0141401 (U.S. Pat. No. 8,568,699) and 2012/0177590 (U.S.P 8,628, 759), and their related patents U.S. Pat. Nos. 8,147,809; 8,071,693; 7,576,210; 7,538,219; 7,417,147; and 7,399,861 are hereby incorporated by reference in their entireties and relied upon.

Sialorrhea is persistent or excessive drooling and can be defined as saliva beyond the margin of the lip. Such drooling after the age of 3 or 4 is considered abnormal and is typically found in subjects who have motor deficiencies or neurological dysfunctions. Sialorrhea is a significant problem in children who have cerebral palsy and in adults who have neurodegenerative disorders (such as Parkinson's disease, ALS or Lou Gehrig's disease, muscular dystrophy or multiple sclerosis). Sialorrhea also affects children with mental retardation and patients of any age who have sustained brain injuries or stroke or who have esophageal cancer or other cancers of the mouth and alimentary canal. Sialorrhea can also result from adverse drug reactions to tranquilizers, anticholinesterases and anticonvulsants.

Sialorrhea can cause various physical and social disabilities, such as chapping of the lips, dehydration, odor, impaired speech, serious feeding and swallowing problems, aspiration, skin, maceration and risk of infection, not to mention embarrassment to the patient and caregiver.

Various approaches to managing treatment of sialorrhea have been proposed, including biofeedback, positive and negative reinforcement, acupuncture, certain anticholinergic medications, botulinum toxin, gastroesophageal reflux control, radiation therapy and surgical options.

With respect to anticholinergic agents, glycopyrrolate has been used in oral tablet form to treat sialorrhea in adults and in children; an oral liquid is also available for pediatric use. Unfortunately, classic side-effects for anticholinergics of constipation, excessive oral dryness, blurred vision, urinary retention, hyperactivity and irritability occur. In clinical trials of the solid oral form in children, most of whom had cerebral palsy, over 20% dropped out of the study because of such adverse effects to the medication. While glycopyrrolate was effective in reducing drooling, such adverse events affected 69% of the children taking the drug. Based on the data, individual doses of about 0.1 mg/kg of glycopyrrolate should show marked improvement in children. [See MIER, RICHARD J. et al., *Arch Pediatr Adolesc Med*, 2000, 154:1214-1218 (American Medical Association, publisher).] In clinical trials of the liquid oral form, more than 85% of the children had cerebral palsy. The maximum recommended dosage of glycopyrrolate was 0.1 mg/kg or 3 mg TID, whichever was lower. The most common adverse events observed were related to glycopyrrolate's mechanism of action as an anticholinergic, as in the earlier studies of the solid form. [See ZELLER, ROBERT S. et al., *Ther Clin Risk Manag*, 2012, 8, 15-23 [Dove Medical Press Ltd., publisher) .] Adults, such as Parkinson's disease patients, typically start at 0.5 mg orally, one to three times daily.

Scopolamine, a topical anticholinergic, has been used to treat sialorrhea in the form of a transdermal patch, but side-effects include pruritus at the patch site, urinary retention, blurred vision, dizziness, irritability and glaucoma. Except for pruritus, these are typical systemic side-effects of anticholinergics. See HOCKSTEIN, et al., *Am Fam Physician*, 2004: 69: 26: 28-34 (American Academy of Family Physicians, publisher.)

Intra-oral tropicamide films have also been proposed for treatment of sialorrhea by temporarily decreasing saliva production in an individual. Tropicamide is an anticholinergic with a relatively rapid onset of action. Quick dissolving film compositions of a number of known anticholinergics including tropicamide are described in Morello et al. United States Patent Application Publication No. US2008/0102102 A1. Clinical trials of an intra-oral film composition of tropicamide in Parkinson's disease patients have also been described. Other intra-oral dosage forms are also described in the Morello et al. document. See also NHOO4—*Treatment of Sialorrhea*, NHOO4 Program Summary—2015, info@neurohealing.com.

WO2001/0008681 A1, published Feb. 8, 2001, describes various methods of administration of glycopyrrolate. To treat sialorrhea, as well as a number of other conditions, systemic administration through the buccal and sublingual membranes is suggested. As noted on page 20 of the WO document, such systemic administration provides a rapid onset of action, provides high blood levels and avoids the first-pass effect. Penetration enhancers can be included to provide improved transmucosal delivery of systemic glycopyrrolate.

Orally disintegrating tablets comprising glycopyrrolate for treating sialorrhea have also been described in Dillaha U.S. Patent Application Publication No. US2008/0260823, published Oct. 23, 2008. The published application claims that the orally disintegrating tablets described therein are especially useful in patients who have difficulty swallowing and disintegrate in a few minutes. There is also a very general suggestion of reduced systemic side-effects, contrary to the teachings of WO2001/0008681; however, in a buccal delivery system, a penetration enhancer is included by Dillaha, which would tend to increase delivery to the bloodstream, not decrease it.

Tapolsky et al. also describe a pharmaceutical carrier device suitable for delivery of pharmaceutical compounds to mucosal surfaces. The device comprises an adhesive layer and a non-adhesive backing layer and the pharmaceutical can be in either or both layers. A method for the transmucosal delivery of a systemic pharmaceutical for achieving a fast onset of activity or a desired level of a systemic pharmaceutical in the blood is claimed. Among the many pharmaceuticals, anticholinergics are mentioned generally.

Saliva has a major role in digestion, lubrication and immunity and in maintaining homeostasis. The major saliva glands which secrete saliva include the parotid (the largest), the submandibular and the sublingual glands. When in the unstimulated state, 70% of saliva is secreted by submandibular and sublingual glands. However, when in the stimulated state, the parotid gland secretes most of the saliva. Sialorrhea can be due to increased production of saliva or it can be caused by failure of the mechanisms that remove or clear saliva from the oral cavity. For example, muscle incoordination inhibits the reflex to swallow. When sialorrhea occurs in patients with neurologic disorders, the condition is usually caused by impaired swallowing. Treatment with anticholinergics have typically, but unfortunately, been limited by their systemic side-effects.

The soft anticholinergic esters of U.S. Pat. Nos. 8,628,729, 8,147,809, 7,576,210 and 7,399,861 have been previously proposed for use in a variety of pharmaceutical forms for various conditions requiring use of a locally active, but not systemically active, anticholinergic agent. That is, these anticholinergics, which are soft drugs, are designed to elicit their desired pharmacological effect at the site of application, but to be quickly metabolized into their designed-in, inactive metabolite upon entering the systemic circulation, affording reduced side-effects. However, these soft anticholinergic agents were never previously proposed for use in the treatment of sialorrhea. This was due to the fact that the esters were found to be very short-acting in mydriatic studies. In the eye, the unique alkyl ester function of these compounds was rapidly hydrolyzed and deactivated, such that activity was very short term. It was taught that the unique alkyl ester function of the soft esters would also be rapidly hydrolyzed and deactivated, so that these compounds would not be useful in the treatment of sialorrhea.

SUMMARY

The subject application concerns methods and intra-oral formulations for treating excessive drooling conditions in subjects, in particular, in humans suffering from sialorrhea. A composition herein comprises at least one soft anticholinergic agent, which is a soft ester analog of glycopyrrolate as described in more detail below, in an effective amount or concentration that inhibits excessive drooling, or sialorrhea. One embodiment is an intra-oral composition comprising: (a) at least one compound having the formula (1):

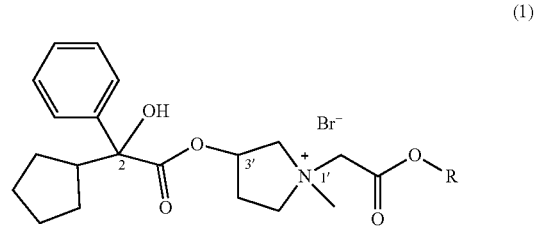

(1)

wherein R is methyl or ethyl, said compound having the R, S, or RS stereoisomeric configuration at the 2 position and 1' and 3' positions, or being a mixture thereof, in an amount effective to inhibit or diminish sialorrhea, and (b) at least one pharmaceutically acceptable carrier or excipient, provided that said intra-oral composition is anhydrous, or that said intra-oral composition is in a solid or film form wherein at least the portion(s) of the composition in contact with said compound is/are anhydrous. In one particular embodiment, R is ethyl and the pharmaceutically acceptable carrier or excipient (b) comprises anhydrous ethanol. Use of at least one compound of formula (1) in the manufacture of an intra-oral composition comprising said at least one carrier or excipient, for treating or inhibiting sialorrhea is still another embodiment.

A preferred embodiment of an intra-oral composition comprises: (a) at least one compound having the following stereospecific formula (2):

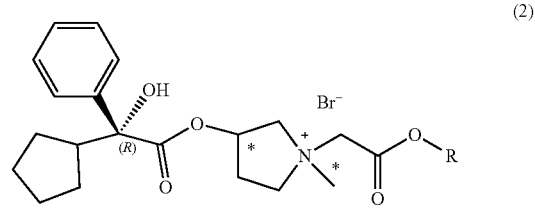

(2)

wherein R is methyl or ethyl, said compound having the R stereoisomeric configuration at the 2 position and having the R, S, or RS stereoisomeric configuration at the 1' and 3' positions (designated by asterisks), or being a mixture thereof, in an amount effective to inhibit or diminish sialorrhea, and (b) at least one pharmaceutically acceptable carrier or excipient, provided that said intra-oral composition is anhydrous, or that said intra-oral composition is in a solid or film form wherein at least the portion(s) of the composition in contact with said compound is/are anhydrous. In one particular embodiment, R is ethyl and the pharmaceutically acceptable carrier or excipient (b) comprises anhydrous ethanol. The amount of compound (2) is sufficient to inhibit sialorrhea. Use of at least one said compound of formula (2) in the manufacture of an intra-oral medicament composition comprising said at least one compound and at least one carrier or excipient, for treating/inhibiting sialorrhea is another embodiment.

Yet another embodiment provides an intra-oral pharmaceutical composition comprising (a) one or more R=ethyl compounds of the foregoing formula (2), (b) anhydrous ethanol and (c) one or more additional pharmaceutically acceptable carriers or excipients, provided that said intra-oral composition is anhydrous, or that said intra-oral composition is in a solid or film form wherein at least the portion(s) of the composition in contact with said compound is/are anhydrous. Yet another embodiment provides an intra-oral composition comprising (a) and (b) as above in this paragraph; (c) optionally, at least one film-forming or gelling or viscosity-controlling or mucoadhesive ingredient; and (d) optionally, at least one additional carrier or excipient; provided that said intra-oral composition is anhydrous, or that said intra-oral composition is in a solid or film form wherein at least the portion(s) of the composition in contact with said compound is/are anhydrous, and comprises an amount of the compound of formula (2) sufficient to significantly diminish excessive drooling, that is, to inhibit sialorrhea. Still another embodiment is use of the compound of formula (2) in the preparation of an intra-oral medicament composition for inhibiting sialorrhea.

Despite the foregoing, while an anhydrous form is appropriate for storage stability, it is not necessary that the intra-oral formulation be anhydrous at the time of administration. For example, a freshly made aqueous solution can be used. Thus, an anhydrous powder or tablet in a sealed aluminum packing dosage form can be dissolved in water or juice and held in the mouth and swished around. An anhydrous ethanolic solution, if too concentrated to be sprayed in the mouth, can be diluted with excess water immediately prior to administration.

Methods of treating or inhibiting or ameliorating excessive drooling, including sialorrhea, using at least one compound of formula (1) or (2) above or an intra-oral composition as described herein, are also included. The methods comprise, for example, administering intra-orally to the oral mucosa (in particular, buccally to the buccal mucosa, sublingually to the sublingual mucosa or lingually to the tongue or gingivally to the gingival mucosa) of a subject suffering from sialorrhea, at least one compound of formula (2) or an intra-oral formulation comprising at least one alkyl ester of formula (2) above and at least one anhydrous pharmaceutically acceptable non-toxic carrier or excipient, provided that said intra-oral formulation is anhydrous, or that said intra-oral formulation is in a solid or film form wherein at least the portion(s) of the composition in contact with said compound is/are anhydrous, and that the amount of the compound of formula (2) is sufficient to significantly diminish excessive drooling, that is, to inhibit sialorrhea. The anhydrous carrier can be or contain ethanol when R is ethyl; if it is not ethanol, it should be chosen such that it will not result in undesirable transesterification of the ethyl ester group.

A composition of the subject application can be formulated as a solid or semi-solid, powder, film composition, gel, cream, lotion, foam, solution, suspension, aerosol, patch, wipes or emulsion, or the like, and is formulated for intra-oral application for the treatment, inhibition or amelioration of sialorrhea. More preferably, a composition as defined above is formulated as an anhydrous intra-oral solid or film composition, or a solid or film composition in which at least the portion(s) which is/are in contact with the active compound is/are anhydrous, which can contain anhydrous ethanol, which can provide certain advantages, including superior stability or increased shelf-life for the composition, as well as the benefit of minimizing or eliminating the need for a separate preservative in the composition.

Additional advantages for an intra-oral anhydrous solid or film composition, or a solid or film composition in which at least the portion(s) which is/are in contact with the active compound is/are anhydrous, herein include properties such as controlled dissolution and absorption times buccally, sublingually, lingually and gingivally, and facilitation of a capability to be dispensed in pre-set amounts of product per application. A particular formulation can further mask stickiness properties that some soft anticholinergics, such as certain compounds described herein, may have.

One exemplary formulation comprises about 0.01% to about 10% of an ethyl ester compound in 90 to 99.99% of the non-aqueous solvent, ethanol. The formulation can further include one or more additional carriers or excipients, such as a film-forming or gelling or viscosity controlling or mucoadhesive excipient, which itself is anhydrous, that is, non-aqueous.

There is thus provided in one aspect herein a method for treating, inhibiting or ameliorating sialorrhea in a subject suffering from sialorrhea, said method comprising intra-orally administering to said subject at least one compound having the formula (1), or an intra-oral composition comprising: (a) at least one compound having the formula (1):

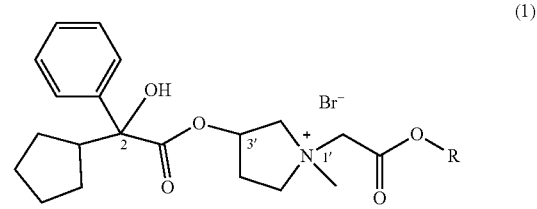

wherein R is methyl or ethyl, said compound having the R, S or RS stereoisomeric configuration at the 2 position and 1' and 3' positions, or being a mixture thereof; (b) optionally, anhydrous ethanol; (c) optionally, at least one gelling or viscosity-controlling or film-forming or mucoadhesive ingredient; and (d) at least one anhydrous pharmaceutically acceptable, non-toxic carrier or excipient; provided that said intra-oral composition or at least the portion(s) thereof in contact with said compound is/are anhydrous; said compound of formula (1) being administered in an amount effective to treat/inhibit sialorrhea of from about 0.01 mg to about 10 mg per dose, up to three times daily. Of particular interest are such intra-oral composition in the form of a solid or film adapted for application to the buccal, sublingual or gingival mucosa.

There is further provided in another aspect herein a method for treating, inhibiting or ameliorating sialorrhea in a subject suffering from sialorrhea, said method comprising intra-orally administering to said subject, at least one compound having the formula (2) below or an intra-oral composition comprising: in an amount effective to treat/inhibit sialorrhea of from about 0.01 mg to about 10 mg per dose, up to three times daily, said compound having the formula (2):

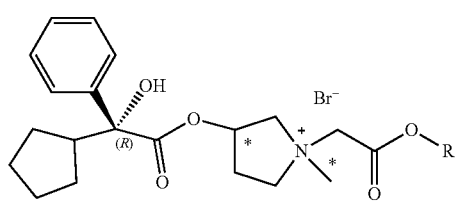

wherein R is methyl or ethyl, said compound having the R stereoisomeric configuration at the 2 position and the R, S, or RS stereoisomeric configuration at the 1' and 3' positions, or being a mixture thereof; said composition comprising (a) said compound; (b) optionally, anhydrous ethanol; (c) optionally, at least one gelling or viscosity-controlling or film-forming or mucoadhesive ingredient; and (d) at least one anhydrous pharmaceutically acceptable, non-toxic carrier or excipient; provided that said intra-oral composition is anhydrous, or that when said composition is a solid or film, at least the portion(s) of the composition in contact with said compound is/are anhydrous. Of particular interest are such intra-oral compositions in the form of a solid or film adapted for application to the buccal, sublingual or gingival mucosa.

Advantageously, the method can surprisingly provide reduction of excessive drooling, as compared to baseline conditions, for at least about six (6) hours by an amount which is substantially equivalent to the reduction of drooling resulting from administration of a composition comprising the same amount of glycopyrrolate, also compared to baseline conditions. The soft esters were previously believed to hydrolyze too rapidly to provide substantially equivalent activity.

The present method is preferably carried out by intra-orally administering the compound or composition to a human subject, to the oral mucosa of the subject. Preferably, the anatomic area for application or administration of the composition is selected from the buccal mucosa, the sublingual mucosa, the tongue and the gingivae, especially the buccal mucosa.

The subject method can reduce saliva production by at least 25%. In some clinical trails of children using glycopyrrolate in treating sialorrhea, saliva reduction was measured using a modified Teacher's Drooling Scale (mTDS). This is a 9 point scale based on the frequency and extent of drooling's effects on clothes and surrounding area. The scale goes from 1 (dry, never drools) through 4-5 (moderate; wet on lips and chin occasionally or frequently) through 7 (severe, drools to the extent that clothing becomes frequently damp) to 9 (profuse, clothing, hands and objects become wet frequently). A decrease of 3 points in this score from baseline has been considered a response to therapy in clinical trials of glycopyrrolate oral solution. Administration of an equal amount of an ester of formula (1) or (2) to glycopyrrolate can provide an equivalent response, but with an improved safety profile, as evidenced by extremely low or even non-existent incidence of the systemic side-effects that plague use of glycopyrrolate. The three point improvement is thus a clinically significant endpoint for an indication for treating sialorrhea.

As previously described, the method can employ the composition formulated as a solid or semisolid, film composition, powder, gel, cream, lotion, foam, solution, suspension, aerosol, patch, wipes or emulsion, or the like and can comprise from about 0.01 mg to about 10 mg of the compound per dose or per unit dosage form. Also as noted previously, the method can employ an aqueous solution (in water or fruit juice, for example) made immediately prior to administration from an anhydrous powder or tablet (for example, in a sealed aluminum package), even from an anhydrous solution or suspension.

A method in accordance with the present description can comprise intra-orally administering to a subject as needed (prn), a composition (anhydrous or not) as defined herein. Administration is preferably one to three times daily, more preferably twice daily, in the morning and afternoon, about 6 to 8 hours apart. A typical single dose for an adult is from about 1 mg to about 10 mg, preferably from about 1 to about 2 mg. For a child, a typical dose is from about 0.02 mg/kg to about 1.0 mg/kg, administered 1, 2 or 3 times per day, preferably 2 times per day.

Surprisingly, the subject method, after single or multiple administrations, can reduce sialorrhea to a clinically effective extent and with fewer systemic side-effects than glycopyrrolate.

A preferred composition herein comprises:
one or more soft esters of formula (1) or (2) as active ingredient; and
at least one anhydrous carrier;
provided that said composition or, in the case of a solid or film, at least the portion(s) thereof in contact with the active ingredient, is/are anhydrous;
or a contemporaneously prepared aqueous solution or suspension as described previously.

As described herein, the subject formulation is preferably a solid or film composition. Accordingly, a more preferred composition comprises: one or more soft esters of formula (1) or (2) as active ingredient; and at least one anhydrous carrier; and
one or more gelling or viscosity-controlling or film-forming or mucoadhesive agents, provided that said formulation is anhydrous or, when the formulation is a solid or film, at least the portions thereof in contact with the active ingredient(s) are anhydrous.

The soft ester of formula (1) or (2) is a soft anticholinergic ester. The absence of water results in much greater storage stability. Suitable anhydrous formulations, and formulations in which the portions thereof which come into contact with the active ingredient are anhydrous, will be described hereinbelow.

Advantageously, when R in formula (1) or (2) is ethyl, anhydrous ethanol can provide for a self-preserving composition, which can provide microbial stability to the composition without added preservatives.

Anhydrous ethanol can also inhibit bacterial growth and provide deodorant properties to the composition.

A further advantage of such a composition according to the present description is provided by the fact that the non-aqueous solvent, anhydrous ethanol, is volatile. Thus, it is possible to use anhydrous ethanol as solvent for the drug in preparation of a layer containing the drug which is then incorporated into the final intra-oral film or solid composition.

A preferred gelling or viscosity-controlling agent can be a modified cellulose, e.g., hydroxypropyl cellulose (HPC), such as the commercially available KLUCEL™, which can preferably provide viscosity of the composition of from about 100 to about 10,000 cps.

DETAILED DESCRIPTION

Throughout this specification and claims, the following definitions, general statements and illustrations are applicable.

The patents, published applications and scientific literature referred to herein establish the knowledge of those with skill in the art and are hereby incorporated by reference in their entireties to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used herein, whether in a transitional phrase or in the body of a claim, the terms "comprise(s)" and "comprising" are to be interpreted as having an open-ended meaning. That is, the terms are to be interpreted synonymously with the phrases "having at least" or "including at least". When used in the context of a process or method, the term "comprising" means that the process or method includes at least the recited steps, but may include additional steps. When used in the context of a composition, the term "comprising" means that the composition includes at least the recited features or components, but may also include additional features or components.

The terms "consists essentially of" or "consisting essentially of" have a partially closed meaning, that is, they do not permit inclusion of steps or features or components which would substantially change the essential characteristics of a process or composition; for example, steps or features or components which would significantly interfere with the desired properties of the compounds or compositions described herein, i.e., the process or composition is limited to the specified steps or materials and those which do not materially affect the basic and novel characteristics of the process or composition.

The terms "consists of" and "consists" are closed terminology and allow only for the inclusion of the recited steps or features or components.

As used herein, the singular forms "a," "an" and "the" specifically also encompass the plural forms of the terms to which they refer, unless the content clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" or "approximately" is used herein to modify a numerical value above and below the stated value by a variance of 20%.

As used herein, the recitation of a numerical range for a variable is intended to convey that the variable can be equal to any values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

In the specification and claims, the singular forms include plural referents unless the context clearly dictates otherwise. As used herein, unless specifically indicated otherwise, the word "or" is used in the "inclusive" sense of "and/or" and not the "exclusive" sense of "either/or."

Technical and scientific terms used herein have the meaning commonly understood by one of skill in the art to which the present description pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10th Ed., McGraw Hill Companies Inc., New York (2001).

As used herein, "treating" means reducing, hindering or inhibiting the development of, controlling, inhibiting, alleviating and/or reversing the symptoms in the individual to which a compound of formula (1) or (2) or a composition comprising a compound of formula (1) or (2) has been administered, as compared to the symptoms of an individual not being administered the compound or composition. A practitioner will appreciate that the combinations, compositions, dosage forms and methods described herein are to be used in concomitance with continuous clinical evaluations by a skilled practitioner (physician or veterinarian) to determine subsequent therapy. Such evaluation will aid and inform in evaluating whether to increase, reduce or continue a particular treatment dose, and/or to alter the mode of administration.

The subject compounds or compositions can also prevent the symptoms, or prevent the occurrence of the symptoms, in the individual to which a composition comprising a compound of formula (1) or (2) above has been administered, as compared to the symptoms of an individual not being administered the compound or composition. This is not a prevention of sialorrhea or excessive drooling in the absolute sense; it does not prevent the medical condition, rather it inhibits the manifestation of the condition for the period of time (hours) for which the administered dose is effective.

The methods described herein are intended for use with any subject/patient that may experience their benefits. Thus, the terms "subjects" as well as "patients," "individuals" and "warm-blooded animals" and "mammals" include humans as well as non-human subjects, such as animals that may experience excessive drooling.

The terms "intra-oral" and "intra-orally" refer to a route of administration in the oral mucosa and mouth cavity, but not extending to the alimentary canal. Intra-oral administration encompasses buccal, lingual, sublingual and gingival administration, that is, buccal administration [to the buccal (cheek) mucosa], lingual administration (to the tongue), sublingual administration to the sublingual mucosa (under the tongue) and gingival administration [to the gingival mucosa (to the gums)].

Compounds useful in a method or composition herein include those of the formula (1):

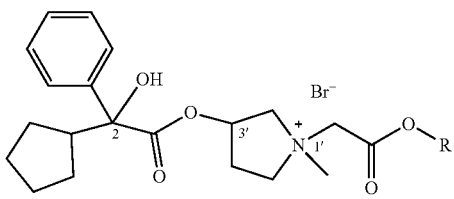

(1)

wherein R is methyl or ethyl and the compound has the R, S, or RS stereoisomeric configuration at the 2 position and at the 1' and 3' positions, or is a mixture thereof.

Compounds having the R configuration with respect to chiral center 2 are of particular interest for use in the instant method and compositions. For example, a preferred compound useful in a method or composition herein has the stereospecific formula (2):

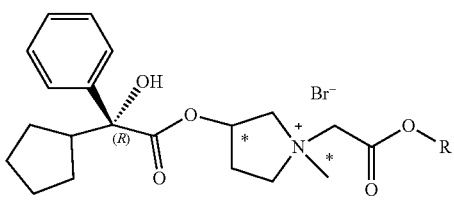

(2)

wherein R is methyl or ethyl, said compound having the R stereoisomeric configuration at the 2 position and the R, S, or RS stereoisomeric configuration at the 1' and 3' positions (designated by asterisks), or being a mixture thereof.

The following compounds are of particular interest for use in a method or composition of the present description:
(i) 3-(2-cyclopentyl-2-phenyl-2-hydroxyacetoxy)-1-(methoxycarbonylmethyl)-1-methylpyrrolidinium bromide;
(ii) 3-(2-cyclopentyl-2-phenyl-2-hydroxyacetoxy)-1-(ethoxycarbonylmethyl)-1-methylpyrrolidinium bromide;
(iii) (2R) 3-(2-cyclopentyl-2-phenyl-2-hydroxyacetoxy)-1-(methoxycarbonylmethyl)-1-methylpyrrolidinium bromide;
(iv) (2R) 3-(2-cyclopentyl-2-phenyl-2-hydroxyacetoxy)-1-(ethoxycarbonylmethyl) methylpyrrolidinium bromide;
(v) (2R,3'R) 3-(2-cyclopentyl-2-phenyl-2-hydroxyacetoxy) (methoxycarbonylmethyl)-1-methylpyrrolidinium bromide;
(vi)(2R,3'S) 3-(2-cyclopentyl-2-phenyl-2-hydroxyacetoxy) (methoxycarbonylmethyl)-1-methylpyrrolidinium bromide;
(vii) (2R,3'R) 3-(2-cyclopentyl-2-phenyl-2-hydroxyacetoxy)-1-(ethoxycarbonylmethyl)-1-methylpyrrolidinium bromide;
(viii) (2R,3'S) 3-(2-cyclopentyl-2-phenyl-2-hydroxyacetoxy)-1-(ethoxycarbonylmethyl)-1-methylpyrrolidinium bromide;
(ix)(2R,1'R,3'S) 3-(2-cyclopentyl-2-phenyl-2-hydroxyacetoxy)-1-(ethoxycarbonylmethyl)-1-methylpyrrolidinium bromide;
(x) (2R,1'S,3'S) 3-(2-cyclopentyl-2-phenyl-2-hydroxyacetoxy)-1-(ethoxycarbonylmethyl)-1-methylpyrrolidinium bromide;
(xi)(2R,1'R,3'R) 3-(2-cyclopentyl-2-phenyl-2-hydroxyacetoxy)-1-(ethoxycarbonylmethyl)-1-methylpyrrolidinium bromide;
(xii) (2R,1'S,3'R) 3-(2-cyclopentyl-2-phenyl-2-hydroxyacetoxy)-1-(ethoxycarbonylmethyl)-1-methylpyrrolidinium bromide;
(xiii) (2R,1'R,3'S) 3-(2-cyclopentyl-2-phenyl-2-hydroxyacetoxy)-1-(methoxycarbonylmethyl)-1-methylpyrrolidinium bromide;
(xiv) (2R,1'S,3'S) 3-(2-cyclopentyl-2-phenyl-2-hydroxyacetoxy)-1-(methoxycarbonylmethyl)-1-methylpyrrolidinium bromide;
(xv) (2R,1'R,3'R) 3-(2-cyclopentyl-2-phenyl-2-hydroxyacetoxy) (methoxycarbonylmethyl)-1-methylpyrrolidinium bromide; and
(xvi) (2R,1'S,3'R) 3-(2-cyclopentyl-2-phenyl-2-hydroxyacetoxy) (methoxycarbonylmethyl)-1-methylpyrrolidinium bromide.

The above compounds (i) to (xvi) can be used alone or two or more of the above compounds can be used in combination in a single composition. Various methods of making the instant compounds are described in the art. A preferred compound for use herein is compound (v) or (vii) above, also known as BOD-06 and BOD-07, respectively.

An anticholinergically effective amount of such an agent inhibits the effect of acetylcholine by blocking its binding to muscarinic cholinergic receptors at neuroeffector sites. Subjects in need of a method of eliciting an anticholinergic response are those suffering from conditions which respond to treatment with an anticholinergic agent, including subjects suffering from excessive drooling or sialorrhea.

The compound of formula (1) or (2) is typically administered in the form of a pharmaceutical composition comprising an anticholinergically effective amount of the compound, anhydrous ethanol and/or other non-toxic pharmaceutically acceptable anhydrous carrier or excipient, provided that the composition itself, or at least the portion(s) of the composition in contact with the compound, is/are also anhydrous. Pharmaceutically acceptable carriers, or diluents, are well-known in the art. The carriers can be any inert material, organic or inorganic, powders, liquid, or gases suitable for administration, such as: alcohol such as hexylene glycol, gelatin, gum arabic, lactose, microcrystalline cellulose, starch, sodium starch glycolate, calcium hydrogen phosphate, magnesium stearate, talcum, colloidal silicon dioxide, and the like, provided that the ingredients or at least those in contact with the compound are anhydrous.

It has been discovered that the instant formulations, having advantageous properties, result when no water or aqueous carrier is added to the formulation. Thus, a composition herein is an anhydrous formulation. By the term "anhydrous", is meant the ordinary scientific meaning of the word, that is, that no water or aqueous excipient is added to the formulation. However, as previously pointed out, at the time of administration, the anhydrous powder, tablet or the like may be dissolved or suspended in water or other aqueous carrier.

The anhydrous compositions can also contain conventional additives such as solvents, stabilizers, wetting agents, emulsifiers, buffers, binders, disintegrants, fragrances, lubricants, glidants, antiadherents, propellants, and the like, just so long as the additives and compositions (or portions thereof in contact with the compound) are anhydrous, that is, free of water to the extent required to avoid significant negative impact on the storage stability of the composition (by hydrolysis of the methyl or ethyl ester drug).

When R in formula (1) or (2) is ethyl, the active ingredient can be readily dissolved in anhydrous ethanol as a solvent, in which the compound is soluble or at least slightly soluble, if desired. At higher concentrations, a suspension or slurry can be prepared, for example an about 15% to about 50% solution or suspension of the ethyl ester in absolute ethanol can be made as part of the preparation of a suitable film composition.

The anhydrous composition herein can be formulated as a solid, semi-solid, or liquid, such as in the form of tablets, film compositions, powders, solutions, lotions, creams, gels, sprays, aerosols, solutions, suspensions or emulsions and the like, and is formulated for intra-oral administration. By way of illustration only, for treating sialorrhea, an intra-oral solid or film composition is often preferred.

In preparing a formulation, it can be appropriate to mill the active compound to provide the correct particle size prior to combining it with the other ingredients. The active compound can be milled to a particle size of less than 200 mesh.

Some examples of suitable intra-oral carriers or excipients, to be added to the compositions herein, include alcohols such as propylene glycol, dimethicone, PGE, allantoin, glycerin, vitamin A and E oils, mineral oil, PPG2, myristyl propionate, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, methyl cellulose and cyclodextrins, including α-, β- and γ-cyclodextrins and their alkylated and hydroxyalkylated derivatives such as randomly methylated β-cyclodextrin, hydroxyethyl-β-cyclodextrin, hydroxyethyl-γ-cyclodextrin, hydroxypropyl-β-cyclodextrin, hydroxypropyl-γ-cyclodextrin, sulfobutylated-β-cyclodextrin and mixtures thereof. β-Cyclodextrin, γ-cyclodextrin and randomly methylated β-cyclodextrin are particularly preferred carriers. The formulations can additionally include: lubricating agents such as talc, magnesium stearate, and mineral oil; wetting agents; emulsifying and suspending agents; and preserving agents such as methyl- and propylhydroxy-benzoates. The compositions can be formulated so as to provide quick, modified or sustained or delayed release or activity of the active ingredient after administration and/or application to the subject by employing procedures known in the art. The use of a separate preserving agent can be avoided by judicious selection of other ingredients, as discussed in more detail below.

The composition can additionally contain one or more optional additives such as colorants, flavoring agents, sweetening agents and the like. In practice, each of these optional additives should be compatible with the active compound. Compatible additives are those that do not prevent the use of or result in the degradation of the compound in the manner described herein.

For purposes of illustration, liquid formulation dosages are expressed based on a percent solution (g/100 ml) or percent concentration (w/v) unless otherwise stated. For solid formulation dosages, the percent concentration can be expressed as mg/mg, or w/w concentrations unless otherwise stated. A person of ordinary skill in the art would readily understand the percent concentration in the context of the type of formulation described.

In general, a therapeutically effective or anticholinergically effective amount of a compound of formula (1) or (2) herein is an amount sufficient to significantly diminish excessive drooling/inhibit sialorrhea. In adult patients, this amount is generally from about 1 mg to about 10 mg, preferably from about 1 mg to about 2 mg, one to three times daily. In children, this amount is generally from about 0.02 mg/kg to about 1.0 mg/kg of body weight, one to three times daily. The exact dosage of a compound in the instant composition can vary depending on its potency, the mode of administration, the application area, the age and weight of the subject and the nature and severity of the condition to be treated.

Administration of a composition as described herein can provide a substantially identical or similar clinical response (decrease in frequency and profuseness of drooling) in a subject, as compared to administration of a composition containing the same concentration of glycopyrrolate. Thus, the results of this discovery are surprising in view of previously published mydriatic studies which suggested that the subject compounds in a composition were required to be present in a concentration from 5 times to 10 times the concentration of a glycopyrrolate composition exhibiting a similar or substantially identical clinical response.

Furthermore, the results of this discovery are especially surprising because the soft alkyl esters were previously believed to hydrolyze too rapidly to be useful in the treatment of sialorrhea. Indeed, it was known that these esters have a half-life in plasma of about 10 minutes and it was believed that they would be hydrolyzed rapidly in the saliva by the enzyme butyrylcholinesterase (BChE). It has now been unexpectedly found that these esters are hydrolyzed by Paraoxonase 1. Although Paraoxonase 2 is present in the saliva, Paraoxonase 1 is not. Therefore, the esters of formula (1) and (2), surprisingly, are not hydrolyzed by the saliva and can be successfully delivered into the oral mucosa (buccally, lingually, sublingually or gingivally) to act in the salivary glands to treat sialorrhea. The absence of Paraoxonase 1 in the salivary glands encourages a particularly long acting activity in treating sialorrhea. At the same time, when the drug does reach the bloodstream, the designed-in breakdown to non-toxic entities by hydrolysis there avoids or greatly minimizes the systemic side-effects which characterize anticholinergics such as glycopyrrolate. Even further, Paraoxonase 1 is also not present in the gastrointestinal tract or in the stomach, which surprisingly permits treatment of conditions such as ulcers, Crohn's disease and ulcerative colitis with the compounds of formula (1) and (2).

Exemplary compositions for use herein in treating sialorrhea can include one or more excipients selected from the group consisting of a plasticizer, a mucoadhesive, a stabilizer, a taste-masking agent (such as a sweetener), a flavor, a breath-freshener, a colorant, an inert filler, a preservative, a nonionic polymer, an anionic polymer, a softener, a swelling agent, a chelating agent, a foaming agent and an effervescing agent. Convenient dosage forms include an oral spray or drop, a film, a candy, a gum, a buccal patch, a lingual tablet, a sublingual tablet and a fast-dissolving tablet, especially a film, a candy (such as a lozenge or lollipop, pastille or troche) and a gum.

Whatever the final dosage form, the readily hydrolyzable nature of the ester of formula (1) or (2) must be taken into acount in the preparation of the dosage form. Care must be taken that the preparation method does not combine the drug with a water-containing ingredient which would hydrolyze the drug during preparation or storage of the dosage form. Further, to avoid introduction of a different, less desirable ester via transesterification, anhydrous ethyl alcohol should be used to dissolve, or at high concentrations suspend, the ethyl ester drug when R is ethyl. This does not mean that ethanol must remain in the final composition, or that water cannot be used in the preparation of non-drug-containing parts of the composition. By way of example, a film or tablet or other dosage form can be prepared in layers. One or more of the layers themselves can have used water or water-containing ingredients in their preparation. After drying, one or more layers can be coated with an absolute (anhydrous)

ethanolic solution or suspension of the drug (the drug being at a concentration of 15% to 50% by weight). The ethanol is then evaporated, leaving a layer of the drug on one or more of the previously constructed layers, which can then be combined. It is also possible to combine the methyl or ethyl ester of formula (1) or (2) with one or more anhydrous cyclodextrins (amorphous or crystalline depending upon the particular one chosen) as identified hereinabove by the kneading method which is well-known in the cyclodextrin art. This method of combination does not introduce water. Other anhydrous carrier ingredients can be introduced during the kneading method or afterwards. The product can be dried and compressed or injection molded or extruded into a dosage form such as an intra-oral (for example, buccal) tablet, which can be packaged in aluminum foil to protect its anhydrous nature. Alternatively, it can be pulverized and used to form a layer in a layered tablet or film, for example, or pulverized and placed in an aluminum foil package to protect its anhydrous nature until administration (at which time it may be mixed with water or other aqueous carrier immediately prior to dosing).

Plasticizers for use in the film compositions described herein can include glycerin, sorbitol, propylene glycol, polyethylene glycol, triacetin, triethyl citrate, acetyl triethyl citrate and other citrate esters.

Stabilizers for use in the film compositions described herein include anti-oxidants, chelating agents and enzyme inhibitors such as ascorbic acid, vitamin E, butylated hydroxyanisole, butylated hydroxytoluene, propyl gallate, dilauryl thiodipropionate, thiodipropionic acid, gum acacia, citric acid and its salts and glutathione.

Film dosage forms can vary in size depending upon placement in the mouth.

Some preferred film dosage forms have an adhesive layer or property, such as a mucoadhesive layer or property, which upon wetting serves to adhere the composition to the epithelial surface of the mouth. An adherent layer can also be designed to preferentially release the compound of formula (1) or (2) to the oral cavity and minimize release of the drug systemically into the bloodstream (where it would be deactivated). Preferably, such adherent dosage forms do not stick to the fingers when dry, in order to facilitate insertion.

Natural and artificial flavors or flavorings that can be used in the film compositions include those known to persons skilled in the art. The flavors will be selected based on their inability to increase the salivatory response and/or their ability to mask the taste of the active agent. Typical flavorings can be selected from synthetic flavor oils, flavoring aromatics, oleo resins and extracts derived from plants, leaves, flowers and fruits. Representative flavor oils include spearmint oil, cinnamon oil, peppermint oil, clove oil, bay oil, thyme oil, cedar leaf oil, oil of nutmeg, oil of sage and oil of bitter almonds. Also useful are artificial, natural or synthetic fruit flavors such as vanilla, chocolate, coffee, cocoa, grape and various citrus oils, such as lemon, orange, lime and grapefruit. Also useful are fruit essences including apple, pear, peach, strawberry, raspberry, cherry, plum, pineapple, apricot and the like. Flavoring agents can also be used individually or in combination. Other flavoring agents that can be used in compositions herein include aldehydes and esters including cinnamyl acetate, cinnamaldehyde, citral, diethylacetal, eugenyl formate, p-methylanisole and the like. Further examples of aldehyde flavorings include, for example, acetaldehyde (apple); benzaldehyde (cherry, almond); cinnamic aldehyde (cinnamon); citral, for example, alpha citral (lemon, lime); neral, that is, beta citral (lemon, lime); decanal (orange, lemon); ethyl vanillin (vanilla, cream); heliotropine, e.g., piperonal (vanilla, cream); vanillin (vanilla, cream); alpha-amyl cinnamaldehyde (spicy fruity flavors); decanal (citrus fruits); aldehyde C-8 (citrus fruits); aldehyde C-9 (citrus fruits); aldehyde C-12 (citrus fruits); 2-ethyl butyraldehyde (berry fruits); hexenal, e.g., trans-2 (berry fruits); tolyl aldehyde (cherry, almond); veratraldehyde (vanilla); 2,6-dimethyl-5-heptenal, e.g., melonal (melon); 2,6-dimethyloctanal (green fruit); and 2-dodecenal (citrus, mandarin); cherry; grape and combinations thereof. In general, any flavoring or food additive, such as those described in *Chemicals Used in Food Processing*, publication 1274 by the National Academy of Sciences, pages 63-258, can be used. The effect of flavors can be enhanced using flavor enhancers such as tartaric acid, citric acid, vanillin, and higher alcohols.

Breath freshening agents of use in the film compositions include menthol and other flavors or fragrances commonly used for oral hygiene or oral cleansing and include various quaternary ammonium bases.

The film compositions can also contain one or more coloring agents (colors, colorants). These colorants are known in art as "FD&C" dyes and lakes.

Nonionic polymers suitable for use in the film compositions include, for example, cellulose polymers such as carboxymethylcellulose, hydroxyethyl cellulose, methylcellulose, hydroxypropyl cellulose and hydroxypropyl methylcellulose; polyvinylpyrrolidone (PVP); polyvinyl alcohol (PVA); polyethylene oxide; modified starch; gelatin; agar; guar gum; locust bean gum; bentonite; and combinations thereof. Preferred nonionic polymers useful in the film compositions are polyvinylpyrrolidone, hydroxypropyl methylcellulose, hydroxypropyl cellulose, polyvinyl alcohol, gelatin, polyethylene oxide or a combination thereof. A nonionic polymer especially useful herein is polyvinyl alcohol, gelatin, hydroxypropyl methylcellulose or a combination thereof. Also highly preferred for use herein are the cyclodextrins mentioned previously.

Anionic polymers useful in the film compositions include polyacrylic acid such as carbopol, polycarbophil, poly(methyl vinyl ether-co-methacrylic acid), poly(2-hydroxyethyl methacrylate), poly(methylmethacrylate), poly(isobutylcyanoacrylate), poly(isohexylcyanoacrylate) and polydimethylaminoethyl methacrylate; acacia; alginate; carrageenan; guar gum derivative; karaya gum; pectin; tragacanth gum; xanthan gum; dextran; sodium carboxymethyl cellulose ("sodium CMC"); hyaluronic acid; and combinations thereof. Preferably, an anionic polymer useful herein is carbopol, polycarbophil, alginate, carrageenan, pectin, sodium CMC or a combination thereof. Most preferably, an anionic polymer useful herein is carbopol, polycarbophil, alginate, carrageenan, sodium CMC or a combination thereof.

Softening agents suitable for use in preparing the film compositions can include propylene glycol, water, polyethylene glycol, glycerin, triacetin, diacetylated monoglycerides, diethyl phthalate, triethyl citrate and combinations thereof. More preferably, a softening agent useful in the compositions is propylene glycol, water, glycerin, polyethylene glycol or a combination thereof. Most preferably, a softening agent suitable for use in the composition is water, propylene glycol, glycerin or a combination thereof. However, as with all the ingredients, care must be taken to remove water or alcohol other than anhydrous ethanol so that the final composition is anhydrous (or at least those portions in contact with the active ingredient), and so that the dangers of hydrolyzing the drug's ester group or exchanging it for a less desirable ester are avoided.

Chelating agents suitable for use in the film include, for example, ethylenediaminetetraacetic acid ("EDTA") and salts thereof such as disodium EDTA, tetrasodium EDTA and calcium disodium EDTA; diethylenetriaminepentaacetic acid ("DTPA") and salts thereof; hydroxyethyl ethylenediaminetriacetic acid ("HEDTA") and salts thereof; nitrilotriacetic acid ("NTA"); and combinations thereof. Preferably, a chelating agent useful herein is EDTA, HEDTA, salts thereof or a combination thereof. Most preferably, a chelating agent useful in the invention is EDTA or a salt thereof.

Another type of film composition provided herein is a water-erodable film device for adhesion to mucosal surfaces, for example, a layered film disk having a backing layer and an adhesive layer and having the compound of formula (1) or (2) in one or more of the layers, or between them.

In another embodiment, the water-erodable film device further comprises a third layer between the first adhesive layer and the second backing layer. The third layer is a water-erodable adhesive layer which has a surface area sufficient to encompass the first adhesive layer and contact the mucosal surface. In this manner, localized delivery of the soft ester can be accomplished in a unidirectional manner toward the mucosal layer.

The adhesive layer(s) comprise(s) a film-forming polymer such as hydroxyethyl cellulose, hydroxypropyl cellulose, hydroxypropylmethyl cellulose, hydroxyethyl methyl cellulose, polyvinyl alcohol, polyethylene glycol, polyethylene oxide, ethylene oxide-propylene oxide co-polymers, collagen and derivatives, gelatin, albumin, polyaminoacids and derivatives, polyphosphazenes, polysaccharides and derivatives, chitin or chitosan, alone or in combination and a bioadhesive polymer such as polyacrylic acid, polyvinyl pyrrolidone or sodium carboxymethyl cellulose, alone or in combination.

The non-adhesive backing layer(s) comprise(s) hydroxyethyl cellulose, hydroxypropyl cellulose, hydroxyethylmethyl cellulose, hydroxypropylmethyl cellulose, polyvinyl alcohol, polyethylene glycol, polyethylene oxide or ethylene oxide-propylene oxide co-polymers, alone or in combination.

In another embodiment, the number of layers of the water-erodable film device can be further varied to adjust the kinetics of the erodability and provide a convenient manner of altering the release of the pharmaceutical and the lifespan of the device.

In a preferred embodiment, the backing layer comprises two or more layers having different erodibility kinetics.

Also, unlike the bioadhesive tablets which are known in the art, the bio-erodable film device herein minimizes the discomfort associated with application of a foreign substance for a period of time sufficient to provide effective drug delivery to the treatment site. Often, users of the bioadhesive tablets of the prior art experience unpleasant sensations due to their solidity, bulkiness and slow dissolution time if erodable, especially when used in the oral cavity. Moreover, because of the typical thickness of bioadhesive tablets, which may or may not be water soluble, the preferred site of application is on the upper gingival area. This site is usually unsatisfactory for local delivery as the type of compounds to be delivered, their bioavailability and pharmokinetics is limited. In contrast to tablets, the film device herein offers the advantages of an effective residence time with minimal discomfort and ease of use, and is an appropriate vehicle for the local delivery of the soft ester, given its thinner, flexible form.

Unlike the film systems known in the art which are used to deliver pharmaceutical through the skin or mucosa, the film device provided herein is made of water-erodable components and thus is bioerodable. The use of water-erodable components allows the device to erode over a period of time, with natural bodily fluids (saliva) slowly dissolving or eroding away the carrier, while the active ingredient remains at the application site. Unlike bandages and other non-water-erodable film systems, the subject or caregiver does not need to remove the film device following treatment. Also, the subject does not experience the sensation of the presence of a foreign object at the mucosal surface or in the mouth, given that upon application, water absorption softens the device, and over time, the device slowly dissolves or erodes away.

The residence time of the instant bio-erodable film device depends on the erosion rate of the water-erodable polymers used in the formulation and their concentrations. The erosion rate can be adjusted, for example, by mixing together components with different solubility properties or chemically different polymers, for example, hydroxyethyl cellulose and hydroxypropyl cellulose; by using different molecular weight grades of the same polymer, for example, mixing low and medium molecular weight hydroxyethyl cellulose; by using excipients or plasticizers of various lipophilicities or water solubility characteristics (including essentially insoluble components); by using water-soluble inorganic and organic salts; by using crosslinking agents such as glyoxal with polymers such as hydroxyethyl cellulose for partial crosslinking; or by post-treatment irradiation or curing, which can alter the physical state of the film, including its crystallinity or phase transition, once obtained. These methods can be employed alone or in combination in order to modify the erosion kinetics of the device.

Upon application, the film delivery device adheres to the mucosal surface and is held in place. Water absorption softens the device, thereby diminishing the foreign body sensation. As the device rests on the mucosal surface, delivery of the drug occurs. Residence times can be adjusted over a wide range depending upon the desired timing of the delivery of the compound and the desired lifespan of the carrier. Preferably, the residence time is adjusted from about 1 hour to about 8 hours.

In one embodiment, there is provided a film disc having an adhesive layer and a non-adhesive backing layer which can be comprised of components having similar or different hydrophilicities. The active ingredient can be included in either layer, although preferably, it is included in the adhesive layer, which is closest to the treatment site and which will have a slower erosion time, given that the backing layer protects the interior, adhesive layer and will typically erode first.

The adhesive layer can comprise at least one film-forming water-erodable polymer (the "film-forming polymer") and at least one pharmacologically acceptable polymer known for its bioadhesive capabilities (the "bioadhesive polymer"). The film forming polymer can comprise hydroxyethyl cellulose, hydroxypropyl cellulose, hydroxypropylmethyl cellulose, hydroxyethyl methyl cellulose, polyvinyl alcohol, polyethylene glycol, polyethylene oxide, ethylene oxide-propylene oxide co-polymers, collagen and derivatives, gelatin, albumin, polyaminoacids and derivatives, polyphosphazenes, polysaccharides and derivatives, chitin and chitosan, alone or in combination. Preferably, the film-forming polymer comprises hydroxyethyl cellulose and hydroxypropyl cellulose. Preferably, in the case of hydroxyethyl cellulose, the average molecular weight (Mw estimated from intrinsic viscosity measurements) is in the range $10^2$ to $10^6$ and more preferably in the range $10^3$ to $10^5$, while in the case of hydroxypropyl cellulose, the average molecular weight (Mw obtained from size exclusion chromatography measurements) is in the range $50 \times 10^3$ to $1.5 \times 10^6$, and more preferably between $80 \times 10^3$ to $5 \times 10^5$.

The bioadhesive polymer of the adhesive layer can comprise polyacrylic acid (PAA), which may or may not be partially crosslinked, sodium carboxymethyl cellulose (NaCMC) and polyvinylpyrrolidone (PVP), or combinations thereof. These bioadhesive polymers are preferred because they have good and instantaneous mucoadhesive properties in a dry, film state. In the case of sodium carboxymethyl cellulose, typical average molecular weights comprise 50,000 to 700,000, and preferably 60,000 to 500,000, with a degree of substitution of 0.7. The substitution range varies between 0.5 and 1.5, and preferably between 0.6 and 0.9. The polyvinyl pyrrolidone can be characterized according to its average molecular weight and is generally between 5,000 and 150,000, preferably between 10,000 and 100,000. The simultaneous use of PAA with some grades of PVP can result in the precipitation of one or both components. This precipitation may not be ideal to obtain a homogenous layer and can slightly alter the overall adhesive properties of the device.

The ratio of the bioadhesive polymer to the film-forming polymer in the adhesive layer can vary, depending on the amount of compound of formula (1) or (2) to be used. However, the content of combined components in the adhesive layer is usually between 5% and 95% by weight, preferably between 10% and 80% by weight. In terms of weight percent of the different bioadhesive polymers PAA, NaCMC and PVP, one skilled in the art will be able to readily adjust the percentages to obtain a film device having the desired characteristics for use herein. Preferred combinations include PAA and NaCMC, NaCMC and PVP, or PAA and PVP, and also include the use of different grades of the same polymer.

The non-adhesive backing layer can comprise a water-erodable, film-forming pharmaceutically acceptable polymer such as hydroxyethyl cellulose, hydroxypropyl cellulose, hydroxypropyl methyl cellulose, hydroxyethyl methyl cellulose, polyvinylalcohol, polyethylene glycol, polyethylene oxide, ethylene oxide-propylene oxide co-polymers, collagen and derivatives, gelatin, albumin, polyaminoacids and derivatives, polyphosphazenes, polysaccharides and derivatives, chitin and chitosan, alone or in combination. The backing layer component may or may not be cross-linked depending on the desired erosion kinetics. In one embodiment, the preferred backing layer component comprises hydroxyethyl cellulose or hydroxypropyl cellulose, and more preferably comprises hydroxyethyl cellulose. Preferably, in the case of hydroxyethyl cellulose, the average molecular weight (Mw estimated from intrinsic viscosity measurements) is in the range $10^2$ to $10^6$, and more preferably in the range $10^3$ to $10^5$, while in the case of hydroxypropyl cellulose, the average molecular weight (Mw obtained from size exclusion chromatography measurements) is in the range of $50 \times 10^3$ to $1.5 \times 10^6$ and more preferably from $80 \times 10^3$ to $5 \times 10^5$.

Moreover, it has been discovered that a particularly preferable combination for the backing layer comprises hydroxypropyl cellulose and an alkylcellulose such as is methylcellulose or ethylcellulose. Such a combination comprises a film-forming amount of alkylcellulose, hydroxypropyl cellulose and a suitable solvent. Advantageously, the film characteristics of the film formed from the gel can be modified depending upon the ratio of hydroxypropyl cellulose to alkylcellulose. Such modifiable characteristics advantageously include the kinetics of erodability.

Typically, the ratio of hydroxypropyl cellulose to alkylcellulose is that necessary to form a suitable film. This ratio can vary based on the other components and the type of alkylcellulose. However, if ethylcellulose is employed then the ratio of hydroxypropyl cellulose to ethyl cellulose is usually from about 1000:1 to about 3:1, preferably from about 200:1 to about 4:1, more preferably from about 200:1 to about 8:1. Typically, as the ratio of hydroxypropyl cellulose to alkylcellulose increases, the water erodability increases, i.e., the films are more readily washed away. Thus, ethylcellulose is a component which acts to adjust the kinetics of erodability of the device.

Crosslinking agents known in the art are appropriate for use in the film device and can include glyoxal, propylene glycol, glycerol, dihydroxy-polyethylene glycol of different sizes, butylene glycol and combinations thereof. The amount of crosslinking agent used can vary, depending on the particular polymers and crosslinking agent but usually should not exceed 5% molar equivalent of the polymeric material, and preferably comprises 0% to 3% molar equivalent of the polymeric material.

Furthermore, in the case of the water-insoluble polymeric materials such as the polyesteraliphatic family (co-polymers of lactide-glycolide, caprolactone etc.) the average molecular weight (Mw) is in the range $10^2$ to $10^5$ and, more preferably, $10^3$ to $10^4$, while in the case of the cellulosic family (ethyl cellulose, cellulose acetate etc.), the average molecular weight (Mw estimated from intrinsic viscosity measurements) is in the range $10^2$ to $10^6$ and more preferably in the range $10^3$ to $10^5$.

Yet another manner of modifying the erosion kinetics of any layer is by employing excipients which plasticize the film concomitantly. The excipient or plasticizer often improves the mechanical properties of the device and/or modifies the active's release profile or disintegation time. Suitable excipients or plasticizers modifying the erosion behavior of the layer(s) can include alkyl-glycols such as propylene glycol, polyethyleneglycols, oleate, sebacate, stearate or esters of glycerol, phthalate and others. Other suitable plasticizers include esters such as acetyl citrate, amyl oleate, myristyl acetate, butyl oleate and stearate, dibutyl sebacate, phthalate esters such as diethyl, dibutyl and diethoxy ethyl phthalate and the like, fatty acids such as oleic and stearic acid, fatty alcohols such as cetyl, myristyl and stearyl alcohol. Moreover, in some instances, a polymer or solvent residual can act as a plasticizer.

It is also possible to modify the erosion kinetics of the film device herein by adjusting the thickness and number of layers. Typically, the thicker the layers, the slower the release of the compound of formula (1) or (2) and the longer the release profile. Correspondingly, the more layers there are, the slower the release of the soft drug and the longer the release profile. In a preferred embodiment, the backing layer comprises two or more layers with different erosion kinetics.

Moreover, combinations of different polymers or similar polymers with definite molecular weight characteristics can be used in order to achieve preferred film forming capabilities, mechanical properties and kinetics of dissolution in any layer. Some combinations for use herein can include ¾ of hydroxyethyl cellulose and ¼ of hydroxypropyl cellulose; ⅘ of low molecular weight hydroxyethyl cellulose and ⅕ of medium molecular weight hydroxyethyl cellulose; and ⅞ of low molecular weight hydroxyethyl cellulose and ⅛ of high molecular weight hydroxyethyl cellulose. Combinations of water-erodable polymers can be employed in order to modify the erosion kinetics of the device. A particularly preferred combination includes ½ hydroxyethyl cellulose, ⅙ hydroxypropylcellulose, and ⅖ of a pseudolatex, i.e. emulsion of polymer, of lactide-glycolide copolymer.

Plasticizers, flavoring and coloring agents, and preservatives can also be included in the instant film delivery device in the adhesive layer, the backing layer, or both. The amounts of each can vary, but typically these components comprise no more than 50%, preferably no more than 30%, most preferably no more than 15% by total weight of the device.

The thickness of the device can vary, depending on the thickness of each of the layers and the number of layers. As stated above, both the thickness and amount of layers can be adjusted in order to vary the erosion kinetics. Preferably, if the device has only two layers, the thickness ranges from 0.05 mm to 3 mm, preferably from 0.1 to 1 mm, and more preferably from 0.1 to 0.5 mm. The thickness of each layer can vary from 10% to 90% of the overall thickness of the layered device, and preferably varies from 30% to 60%. Thus, the preferred thickness of each layer can vary from 0.01 mm to 0.9 mm, and more preferably from 0.03 to 0.6 mm.

While the film device only requires two layers, i.e., an adhesive layer and a backing layer, it is often preferable to have additional layers. One instance in which this can be advantageous is when specific unidirectional flow of the compound of formula (1) or (2) is required toward a mucosal layer. The layered device described above provides some directional release, i.e., release will mainly be toward the mucosa and not, for instance, into the oral cavity. However, due to the swelling characteristics of the thin film, a small amount of soft drug can also be released through the sides of the device and the backing layer if all the layers are of approximately the same surface area and are essentially on top of one another.

In such instances when unidirectional release is desired, an additional layer can be placed between the first adhesive layer and the second backing layer. The third layer is a water-erodable adhesive layer which has a surface area sufficient to encompass said first adhesive layer and contact the mucosal surface. The third layer can be comprised of any of the components described above for the first adhesive layer and thus can be the same or different than the first adhesive layer.

If a bioadhesive layer is to be of a smaller surface area than the other layers, then it is usually between about 5% and about 50%, preferably between about 10% and about 30% smaller than the other layers.

Another suitable dosage form herein is an intra-oral tablet that disintegrates following contact with saliva to deliver the soft methyl or ethyl ester into the oral mucosa and salivary glands.

Since the intra-orally disintegrating tablet disintegrates or dissolves in the mouth, the taste of the soft drug and other accessory ingredients is preferably masked. Taste masking can be achieved in any suitable manner, including the addition of flavoring agents and/or sweeteners, roller compaction with other excipients to minimize the presented surface area of the soft drug, spray drying, sealing with a suitable coating material (e.g., hydroxypropyl methylcellulose, ethylcelluclose, methacrylates, Kollicoat™ and polyvinylpyrrolidone), and encapsulation. Kollicoat™ comprises a copolymer of methylacrylic acid and ethyl acrylate.

For example, fine granules of the drug and disintegrant (e.g., low substituted hydroxypropyl cellulose) can be coated with a water-insoluble polymer (e.g., ethylcellulose) to mask the taste of the soft drug.

Suitable flavoring agents include those described hereinabove. The flavoring agent or mixture thereof typically is present in an amount of about 0.0001% by weight to about 5% by weight.

Suitable sweeteners include, for example, sugars such as sucrose, lactose and glucose, cyclamate and salts thereof, saccharin and salts thereof, ammonium glycyrrhizinate and aspartame. Other possible sweeteners are sucralose and stevia. The sweetener or mixtures thereof typically is/are present in an amount of about 0.001% by weight to about 70% by weight.

The intra-orally disintegrating tablets can be prepared by methods well known in the art of pharmacy, for example, using methods such as those described in Remington: The Science and Practice of Pharmacy, 21st Edition. Philadelphia, Pa.: Lippincott Williams & Wilkins, 2005. Such methods include the step of bringing into association with the active ingredient a carrier (i.e., a pharmaceutically acceptable carrier) which constitutes one or more accessory ingredients. Such accessory ingredients include those conventional in the art, such as, fillers (e.g., polyhydric alcohols, such as mannitol, sorbitol and xylitol, or mixtures thereof); binders (e.g., acacia, tragacanth, gelatin, sucrose, pre-gelatinized starch, starch, sodium alginate, methylcellulose, sodium carboxymethyl cellulose, ethyl cellulose, hydroxypropylmethyl cellulose, polyvinylpyrrolidone and polyacrylamide); diluents; disintegrants; lubricants (e.g., talc, magnesium stearate, mineral oil and mixtures thereof); colorants; flavoring agents; preservatives (e.g., alkyl hydroxbenzoates or salts thereof, such as methyl, ethyl, propyl and/or butyl hydroxybenzoates; sorbic acid or a salt thereof; benzoic acid or a salt thereof and mixtures thereof); wetting agents; and cyclodextrins, especially β-cyclodextrin, γ-cyclodextrin and randomly methylated β-cyclodextrin.

In particular, the intra-oral disintegrating tablet can be prepared by processes, including, but not limited to, tablet molding, direct compression, mass extrusion, and microencapsulation.

Direct compression can be applied to intra-orally disintegrating tablets if disintegrants and/or sugar-based excipients are included in the tableting process. Methods of preparing orally disintegrating tablets by direct compression are known in the art. Microcrystalline cellulose, cross-linked carboxymethyl cellulose sodium, cross-linked polyvinyl pyrrolidone and low or partially substituted hydroxypropyl cellulose absorb water and swell due to capillary action, making them effective disintegrants in the preparation of intra-orally disintegrating tablets. Agar powder also can be used as a disintegrant because the powder absorbs water and swells considerably without forming a gel at physiological temperatures. Sugar-based excipients, such as dextrose, fructose, isomalt, maltitol, maltose, mannitol, sorbitol, starch hydrolysates, polydextrose and xylitol, also can be used in the direct compression process to afford aqueous solubility and sweetness. Furthermore, the fast disintegration of tablets can be achieved, if desired, by incorporating effervescent disintegrating agents, which generate gas.

Suitable effervescent disintegrating agents include agents that evolve gas by means of a chemical reaction that takes place upon exposure of the effervescent disintegrating agent to water in the saliva in the mouth. The reaction is most often a result of the reaction of a soluble acid source and an alkali monocarbonate or carbonate source, which produces carbon dioxide gas upon contact with the water in the saliva. The acid sources can be any that are safe for human consumption including citric acid, tartaric acid, malic acid, fumeric acid, adipic acid and succinic acid. Carbonate sources include dry solid carbonate and bicarbonate salt, such as sodium bicarbonate, sodium carbonate, potassium bicarbonate, potassium carbonate and magnesium carbonate. Reactants that generate oxygen or other gases that are safe for human consumption also are suitable.

In another embodiment, the intra-orally disintegrating tablet for administration herein, preferably for buccal delivery systems, comprises an adhesive layer comprising a hydrophilic polymer with one surface adapted to contact a first tissue of the oral cavity and adhere thereto when wet and an opposing surface in contact with and adhering to an adjacent drug layer comprising the soft ester composition. The drug layer contacts and is in drug transfer relationship with the buccal mucosa when the adhesive layer contacts and adheres to the first tissue, preferably the gingiva. Typically the hydrophilic polymer comprises compounds selected from the group consisting of hydroxypropyl cellulose, hydroxypropyl methylcellulose, hydroxyethylcellulose, ethylcellulose, carboxymethyl cellulose, dextran, guar gum, polyvinyl pyrrolidone, pectins, starches, gelatin, casein, acrylic acid polymers, polymers of acrylic acid esters, acrylic acid copolymers, vinyl polymers, vinyl copolymers, polymers of vinyl alcohols, alkoxy polymers, polyethylene oxide polymers, polyethers and mixtures thereof.

The adhesive layer can additionally contain one or more members including, for example, fillers, tableting excipients, lubricants, flavors, and dyes. The drug layer additionally can contain one or members, such as tableting excipients, fillers, flavors, taste-masking agents, dyes, stabilizers, enzyme inhibitors, and lubricants.

The following EXAMPLES further illustrate compositions described herein. These are illustrative and are not to be considered limiting in any way whatsoever, as many modifications in materials and methods will be apparent to those skilled in the art.

EXAMPLE 1

77.8 Grams of polyethylene oxide are mixed using a mechanical mixer, and the following additional ingredients are added during mixing: compound (v), i.e., BOD-06, or compound (vii), i.e. BOD-07 (5.5 g), peppermint (3.7 g). propylene glycol (3.7 g), aspartame (3.0 g), citric acid (2.6 g), polyoxyethylene hydrogenated castor oil CREMOPHOR™ EL40 (3.7 g) and benzoic acid (0.05 g). The blend is allowed to mix while being maintained at about 70° C. until uniform. It is then forced through an extrusion die to form a film 0.125 mm thick. The film is then cut unto dosage forms ready for packaging.

EXAMPLE 2

A preparation of a backing layer using 42.49% by weight of water, 43.49% by weight of ethyl alcohol, 0.02% of FD&C red dye 40, 10% by weight of hydroxyethyl cellulose (molecular weight $9\times10^4$), 4% by weight of hydropropylcellulose (molecular weight $5\times10^5$) is coated using a knife over roll technique. Then directly on the top of the previous dry film (first layer was 0.07 mm thick), a backing preparation made from 42.49% by weight of water, 42.49% by weight of ethyl alcohol, 0.02% of FD&C red dye 40, 12% by weight of hydroxyethyl cellulose (molecular weight $9\times10^4$) and 3% by weight of oleic acid, is casted and dried. The resulting bilayer backing film is 0.15 mm thick.

EXAMPLE 3

A preparation for the adhesive layer is made using 45.6% by weight water USP, 45% by weight of ethyl alcohol, 2% by weight hydroxyethyl cellulose, NATROSOL® 99-250 L NF (Aqualon), 2.9% by weight polyacrylic acid, NOVEON® AA1 USP (BF Goodrich), and 4.5% by weight of sodium carboxymethyl cellulose, cellulose gum 7 LF PH (Aqualon). This preparation is a bioadhesive preparation but does not contain any active ingredient.

EXAMPLE 4

A 100 ml solution for the adhesive layer is made using 45.1% by weight of water USP, 46% by weight of ethyl alcohol, 1.8% by weight hydroxyethyl cellulose, NATROSOL® 99-250 L NF (Aqualon), 2.6% by weight polyacrylic acid, NOVEON® AA1 USP (BF Goodrich), 4.5% sodium carboxymethyl cellulose, cellulose gum 7 LF PH (Aqualon).

EXAMPLE 5

The film obtained following EXAMPLE 2 is used as substrate for the final multilayer film of this example. The bioadhesive preparation of EXAMPLE 3 is directly casted onto the film of EXAMPLE 2 and dried. A trilayer film is thus obtained, the last layer being bioadhesive but not containing any active. Then the preparation of EXAMPLE 4 is coated using a mask and dried (the mask is a 0.500 mm polyester film in which ellipsoids have been die cut deposited on the trilayer laminate). Then a solution of compound (vii), i.e. BOD-07, 20% by weight in anhydrous ethanol, is applied and allowed to dry. One or both of the preceding steps can be repeated if necessary. The mask is then delaminated. The resulting film is a multi-layer film composed of a laminate backing layer and a laminate bioadhesive layer in which the final component includes the active and is of a smaller surface. With this system, diffusion by either the sides or the back side is limited and allows an unidirectional release of the active ingredient into the mucosal tissues.

EXAMPLE 6

A gel for the backing layers is prepared which contains 79.44% water, 0.01% FD&C red dye 40, 0.05% sodium benzoate, 2.5% peppermint flavor, 13.5% hydroxyethyl cellulose, and 4.5% hydroxypropyl cellulose by weight. The gel is then made into a two layer flexible backing film of 0.17 mm in thickness by first coating a 0.8 mm thick layer of the formulation on a substrate and then drying it at 80° C. for 8 minutes. A second 0.8 mm thick layer is then coated directly on top of the first layer and dried at 80° C. for 8 minutes.

A gel for the bioadhesive layers is prepared which contains 45.2% water USP, 47.2% ethyl alcohol, 1.6% hydroxyethyl cellulose, 0.6% hydroxypropyl cellulose, 2.8% polyacrylic acid NOVEON® AA1 USP, 2.5% sodium carboxymethyl cellulose, and 0.1% titanium dioxide, by weight. Using the gel, a first bioadhesive layer of 0.5 mm is coated directly on top of the two layer flexible backing film and dried at 60° C. for 8 minutes or until sufficient water is removed. Then a solution of compound (vii), i.e. BOD-07, dissolved at 20% by weight in anhydrous ethanol, is applied and dried to evaporate ethanol. A second bioadhesive layer of 0.7 mm is then coated directly on top of the layer of BOD-07 and dried at 60° C. for 20 minutes, or to evaporation of sufficient water.

EXAMPLE 7

A gel for the backing layers is prepared which contains 42.49% water, 42.49% ethyl alcohol, 0.02% of FD&C red dye 40, 14% hydroxyethyl cellulose (mw 9×10$^4$), and 1% sweet peppermint by weight. Using the gel, a first backing layer of 0.7 mm is coated onto a substrate using a knife over roll technique. The layer is dried at 60° C. for 8 minutes. A second backing layer of 0.8 mm is then coated directly on top of the first backing layer and dried at 60° C. for 8 minutes, or until sufficient water is removed. The final two layer film backing is about 0.20 mm in thickness.

A gel for the bioadhesive layers is prepared which contains 45.95% water USP, 46.85% ethyl alcohol, 1.6% hydroxyethyl cellulose NATROSOL® 99-250 L NF (Aqualon), 2.2% polyacrylic acid NOVEON® AA1 USP (BF Goodrich), and 3.4% sodium carboxymethyl cellulose cellulose gum 7 LF PH (Aqualon) by weight. Using the gel, a first bioadhesive layer of 0.5 mm is coated onto the two backing layers and dried at 60° C. for 10 minutes, or until removal of water. Then a mixture of compound (vii) or BOD-07, dissolved at 20% by weight in anhydrous ethanol is applied and dried to evaporate ethanol. A second bioadhesive layer of 0.8 mm is coated onto the layer of compound (vii) and dried at 60° C. for 20 minutes, or until removal of sufficient water.

EXAMPLE 8

500 mg of BOD-06 is mixed with 5 g of β-cyclodextrin, distributed into aluminum pouches, each containing 5 mg BOD-06 and 50 mg β-cyclodextrin, and sealed. Immediately prior to use, the contents of the pouch are dissolved in 50 ml of water and rinsed/swished in the mouth.

EXAMPLE 9

500 mg of BOD-07 is mixed with 5 g of γ-cyclodextrin, distributed into aluminum pouches, each containing 5 mg of BOD-07 and 50 mg γ-cyclodextrin, and sealed. Immediately before administration, the contents of the pouch are dissolved in 50 ml of water and rinsed or swished in the mouth.

EXAMPLE 10

The following ingredients are blended using a V-Blender with an intensifier bar and mixed for about five to ten minutes:

| Ingredient | Amount |
| --- | --- |
| BOD-06 or BOD-07 | 2.0 g |
| Sorbitol N.F. | 988.0 g |
| Sodium Dodecyl Sulfate | 10.0 g |
| | 1000.0 g |

Tablets weighing about 0.05 g/tablet are formed using a compression force of about 1000 psi. These are suitable for buccal use.

EXAMPLE 11

All of the ingredients listed below are blended and then tableted by a direct tableting method with a rotary type tableting machine with a molding punch having a beveled edge, 10 mm in diameter, at a pressure of 1.2 ton/cm$^2$, to provide buccal tablets each weighing 400 mg and containing 5 mg of active ingredient:

| Ingredient | Amount |
| --- | --- |
| BOD-06 or BOD-07 | 10 g |
| Erythritol | 255 g |
| Mannitol | 255 g |
| Crystalline cellulose | 240 g |
| Crospovidone or croscarmellose sodium | 40 g |
| | 800 g |

While certain preferred and alternative embodiments have been set forth for purposes of disclosure, modifications to the disclosed embodiments will occur to those skilled in the art. Accordingly, this specification is intended to cover all embodiments and combinations and modifications thereof which do not depart from the spirit and scope of the following claims.

What is claimed is:

1. An intra-oral composition, said composition comprising:
   (a) at least one compound having the formula:

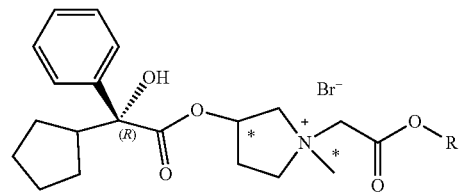

(2)

wherein R is methyl or ethyl, said compound having the R stereoisomeric configuration at the 2 position and the R, S or RS stereoisomeric configuration at the 1' and 3' positions, or being a mixture thereof; and
   (b) at least one anhydrous, non-toxic pharmaceutically acceptable carrier or excipient, wherein the carrier or excipient is suitable for intra-oral administration;
provided that said intra-oral composition is anhydrous; and that said intra-oral composition comprises an anti-excessive-salivation effective amount of from about 1 mg to about 10 mg per adult dose of the compound of formula (2), or from about 0.02 mg/kg to about 1.0 mg/kg per pediatric dose of the compound of formula (2).

2. The intra-oral composition according to claim 1, wherein the intra-oral composition is stable for delivery to human saliva.

3. The intra-oral composition according to claim 1, wherein the intra-oral composition is stable in human saliva for at least about 10 minutes.

4. The intra-oral composition according to claim 1, wherein the intra-oral composition delivers the compound to the intra-oral cavity for interaction with the salivary glands and for rapid systemic hydrolysis.

5. The intra-oral composition according to claim 1, wherein the intra-oral composition is in the form of a solid or film.

6. The intra-oral composition according to claim 1, wherein the intra-oral composition is in the form of an anhydrous powder or tablet.

7. The intra-oral composition according to claim 1, wherein the intra-oral composition is in the form of a semi-liquid or liquid.

8. The intra-oral composition according to claim 7, wherein the intra-oral composition is in the form of a solution, lotion, cream, foam, gel, spray, aerosol, suspension, emulsion, and/or combinations thereof.

9. The intra-oral composition according to claim 1, wherein (b) is anhydrous ethanol.

10. The intra-oral composition according to claim 1, wherein the intra-oral composition is in the form of an oral drop, a buccal film or in the form of an intra-oral solid which is a candy or gum, a lingual tablet, a sublingual tablet, or a fast-dissolving tablet.

11. The intra-oral composition according to claim 1, wherein the intra-oral composition is capable of being mixed with an aqueous solution.

12. The intra-oral composition according to claim 1, wherein said composition further comprises at least one gelling or viscosity-controlling or film-forming or mucoadhesive ingredient, and/or wherein the carrier or excipient comprises a cyclodextrin.

13. The intra-oral composition according to claim 1, wherein the compound of formula (2) is selected from the group consisting of:
- (iii) (2R) 3-(2-cyclopentyl-2-phenyl-2-hydroxyacetoxy)-1-(methoxycarbonylmethyl)-1-methylpyrrolidinium bromide;
- (iv) (2R) 3-(2-cyclopentyl-2-phenyl-2-hydroxyacetoxy)-1-(ethoxycarbonylmethyl)-1-methylpyrrolidinium bromide;
- (v) (2R,3'R) 3-(2-cyclopentyl-2-phenyl-2-hydroxyacetoxy)-1-(methoxycarbonylmethyl)-1-methylpyrrolidinium bromide;
- (vi) (2R,3'S) 3-(2-cyclopentyl-2-phenyl-2-hydroxyacetoxy)-1-(methoxycarbonylmethyl)-1-methylpyrrolidinium bromide;
- (vii) (2R,3'R) 3-(2-cyclopentyl-2-phenyl-2-hydroxyacetoxy)-1-(ethoxycarbonylmethyl)-1-methylpyrrolidinium bromide;
- (viii) (2R,3'S) 3-(2-cyclopentyl-2-phenyl-2-hydroxyacetoxy)-1-(ethoxycarbonylmethyl)-1-methylpyrrolidinium bromide;
- (ix) (2R,1'R,3'S) 3-(2-cyclopentyl-2-phenyl-2-hydroxyacetoxy)-1-(ethoxycarbonylmethyl)-1-methylpyrrolidinium bromide;
- (x) (2R,1'S,3'S) 3-(2-cyclopentyl-2-phenyl-2-hydroxyacetoxy)-1-(ethoxycarbonylmethyl)-1-methylpyrrolidinium bromide;
- (xi) (2R,1'R,3'R) 3-(2-cyclopentyl-2-phenyl-2-hydroxyacetoxy)-1-(ethoxycarbonylmethyl)-1-methylpyrrolidinium bromide;
- (xii) (2R,1'S,3'R) 3-(2-cyclopentyl-2-phenyl-2-hydroxyacetoxy)-1-(ethoxycarbonylmethyl)-1-methylpyrrolidinium bromide;
- (xiii) (2R,1'R,3'S) 3-(2-cyclopentyl-2-phenyl-2-hydroxyacetoxy)-1-(methoxycarbonylmethyl)-1-methylpyrrolidinium bromide;
- (xiv) (2R,1'S,3'S) 3-(2-cyclopentyl-2-phenyl-2-hydroxyacetoxy)-1-(methoxycarbonylmethyl)-1-methylpyrrolidinium bromide;
- (xv) (2R,1'R,3'R) 3-(2-cyclopentyl-2-phenyl-2-hydroxyacetoxy)-1-(methoxycarbonylmethyl)-1-methylpyrrolidinium bromide; and
- (xvi) (2R,1'S,3'R) 3-(2-cyclopentyl-2-phenyl-2-hydroxyacetoxy)-1-(methoxycarbonylmethyl)-1-methylpyrrolidinium bromide.

14. The intra-oral composition according to claim 1, wherein the compound of formula (2) is (2R,3'R) 3-(2-cyclopentyl-2-phenyl-2-hydroxyacetoxy)-1-(ethoxycarbonylmethyl)-1-methylpyrrolidinium bromide or (2R,3'R) 3-(2-cyclopentyl-2-phenyl-2-hydroxyacetoxy)-1-(methoxycarbonylmethyl)-1-methylpyrrolidinium bromide.

15. The intra-oral composition according to claim 1, wherein the compound of formula (2) is from about 1% to about 20% of the composition.

16. The intra-oral composition according to claim 1, wherein the excipient comprises a flavoring agent, taste masking agent, sweeteners, and/or combinations thereof.

17. The intra-oral composition according to claim 1, wherein the composition is in the form of a buccal film or in the form of an intra-oral solid, which is a candy or gum.

18. The intra-oral composition according to claim 7, wherein the gelling or viscosity-controlling or film-forming or mucoadhesive ingredient is hydroxypropyl cellulose, and/or wherein the cyclodextrin comprises one or more members selected from the group consisting of α-cyclodextrin, β-cyclodextrin, γ-cyclodextrin, randomly methylated β-cyclodextrin, hydroxypropyl-β-cyclodextrin, hydroxyethyl-β-cyclodextrin, hydroxypropyl-γ-cyclodextrin, hydroxyethyl-γ-cyclodextrin and sulfobutylated-β-cyclodextrin.

19. The intra-oral composition according to claim 7, wherein the compound of formula (2) is selected from the group consisting of:
- (iii) (2R) 3-(2-cyclopentyl-2-phenyl-2-hydroxyacetoxy)-1-(methoxycarbonylmethyl)-1-methylpyrrolidinium bromide;
- (iv) (2R) 3-(2-cyclopentyl-2-phenyl-2-hydroxyacetoxy)-1-(ethoxycarbonylmethyl)-1-methylpyrrolidinium bromide;
- (v) (2R,3'R) 3-(2-cyclopentyl-2-phenyl-2-hydroxyacetoxy)-1-(methoxycarbonylmethyl)-1-methylpyrrolidinium bromide;
- (vi) (2R,3'S) 3-(2-cyclopentyl-2-phenyl-2-hydroxyacetoxy)-1-(methoxycarbonylmethyl)-1-methylpyrrolidinium bromide;
- (vii) (2R,3'R) 3-(2-cyclopentyl-2-phenyl-2-hydroxyacetoxy)-1-(ethoxycarbonylmethyl)-1-methylpyrrolidinium bromide;
- (viii) (2R,3'S) 3-(2-cyclopentyl-2-phenyl-2-hydroxyacetoxy)-1-(ethoxycarbonylmethyl)-1-methylpyrrolidinium bromide;
- (ix) (2R,1'R,3'S) 3-(2-cyclopentyl-2-phenyl-2-hydroxyacetoxy)-1-(ethoxycarbonylmethyl)-1-methylpyrrolidinium bromide;
- (x) (2R,1'S,3'S) 3-(2-cyclopentyl-2-phenyl-2-hydroxyacetoxy)-1-(ethoxycarbonylmethyl)-1-methylpyrrolidinium bromide;
- (xi) (2R,1'R,3'R) 3-(2-cyclopentyl-2-phenyl-2-hydroxyacetoxy)-1-(ethoxycarbonylmethyl)-1-methylpyrrolidinium bromide;
- (xii) (2R,1'S,3'R) 3-(2-cyclopentyl-2-phenyl-2-hydroxyacetoxy)-1-(ethoxycarbonylmethyl)-1-methylpyrrolidinium bromide;
- (xiii) (2R,1'R,3'S) 3-(2-cyclopentyl-2-phenyl-2-hydroxyacetoxy)-1-(methoxycarbonylmethyl)-1-methylpyrrolidinium bromide;
- (xiv) (2R,1'S,3'S) 3-(2-cyclopentyl-2-phenyl-2-hydroxyacetoxy)-1-(methoxycarbonylmethyl)-1-methylpyrrolidinium bromide;
- (xv) (2R,1'R,3'R) 3-(2-cyclopentyl-2-phenyl-2-hydroxyacetoxy)-1-(methoxycarbonylmethyl)-1-methylpyrrolidinium bromide; and (xvi) (2R,1'S,3'R) 3-(2-cyclopentyl-2-phenyl-2-hydroxyacetoxy)-1-(methoxycarbonylmethyl)-1-methylpyrrolidinium bromide.

20. The intra-oral composition according to claim 7, wherein the compound of formula (2) is (2R,3'R) 3-(2-cyclopentyl-2-phenyl-2-hydroxyacetoxy)-1-(ethoxycarbonylmethyl)-1-methylpyrrolidinium bromide or (2R,3'R) 3-(2-cyclopentyl-2-phenyl-2-hydroxyacetoxy)-1-(methoxycarbonylmethyl)-1-methylpyrrolidinium bromide.

21. The intra-oral composition according to claim 7, wherein the compound of formula (2) is from about 1% to about 20% of the composition.

22. The intra-oral composition according to claim 7, wherein the composition is in the form of a buccal film or in the form of an intra-oral solid which is a candy or gum.

23. The intra-oral composition according to claim 14, wherein the gelling or viscosity-controlling or film-forming or mucoadhesive ingredient is hydroxypropyl cellulose, and/or wherein the cyclodextrin comprises one or more members selected from the group consisting of α-cyclodextrin, β-cyclodextrin, γ-cyclodextrin, randomly methylated β-cyclodextrin, hydroxypropyl-β-cyclodextrin, hydroxyethyl-β-cyclodextrin, hydroxypropyl-γ-cyclodextrin, hydroxyethyl-γ-cyclodextrin and sulfobutylated-β-cyclodextrin.

24. The intra-oral composition according to claim 14, wherein the composition is in the form of a buccal film or in the form of an intra-oral solid which is a candy or gum.

25. The intra-oral composition according to claim 15, wherein the composition is in the form of a buccal film or in the form of an intra-oral solid which is a candy or gum.

26. The intra-oral composition according to claim 17, wherein the composition is in the form of a buccal film or in the form of an intra-oral solid which is a candy or gum.

27. The intra-oral composition according to claim 22, wherein the composition is in the form of a buccal film or in the form of an intra-oral solid which is a candy or gum.

28. An intra-oral composition, said composition comprising:
    (a) at least one compound having the formula:

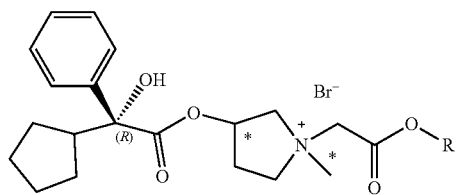

wherein R is methyl or ethyl, said compound having the R stereoisomeric configuration at the 2 position and the R, S or RS stereoisomeric configuration at the 1' and 3' positions, or being a mixture thereof; and
    (b) the dried residue of an about 15% to about 50% solution or suspension of the compound of formula (2) in an anhydrous ethanol, wherein the dried residue is suitable for intra-oral administration;
provided that said intra-oral composition or at least the portion(s) thereof which is/are in contact with said compound, is/are anhydrous and that said composition comprises from about 0.02 mg/kg to about 1.0 mg/kg per pediatric dose of the compound of formula (2), said composition being in the form of a solid or film.

29. The intra-oral composition according to claim 28, wherein the intra-oral composition is stable for delivery to human saliva.

30. The intra-oral composition according to claim 28, wherein the intra-oral composition is stable in human saliva for at least about 10 minutes.

31. The intra-oral composition according to claim 28, wherein the intra-oral composition delivers the compound to the intra-oral cavity for interaction with the salivary glands and for rapid systemic hydrolysis.

32. The composition according to claim 28, wherein said composition further comprises at least one gelling or viscosity-controlling or film-forming or mucoadhesive ingredient, and/or wherein the carrier or excipient comprises a cyclodextrin.

33. The intra-oral composition according to claim 28, wherein the compound of formula (2) is selected from the group consisting of:
    (iii) (2R) 3-(2-cyclopentyl-2-phenyl-2-hydroxyacetoxy)-1-(methoxycarbonylmethyl)-1-methylpyrrolidinium bromide;
    (iv) (2R) 3-(2-cyclopentyl-2-phenyl-2-hydroxyacetoxy)-1-(ethoxycarbonylmethyl)-1-methylpyrrolidinium bromide;
    (v) (2R,3'R) 3-(2-cyclopentyl-2-phenyl-2-hydroxyacetoxy)-1-(methoxycarbonylmethyl)-1-methylpyrrolidinium bromide;
    (vi) (2R,3'S) 3-(2-cyclopentyl-2-phenyl-2-hydroxyacetoxy)-1-(methoxycarbonylmethyl)-1-methylpyrrolidinium bromide;
    (vii) (2R,3'R) 3-(2-cyclopentyl-2-phenyl-2-hydroxyacetoxy)-1-(ethoxycarbonylmethyl)-1-methylpyrrolidinium bromide;
    (viii) (2R,3'S) 3-(2-cyclopentyl-2-phenyl-2-hydroxyacetoxy)-1-(ethoxycarbonylmethyl)-1-methylpyrrolidinium bromide;
    (ix) (2R,1'R,3'S) 3-(2-cyclopentyl-2-phenyl-2-hydroxyacetoxy)-1-(ethoxycarbonylmethyl)-1-methylpyrrolidinium bromide;
    (x) (2R,1'S,3'S) 3-(2-cyclopentyl-2-phenyl-2-hydroxyacetoxy)-1-(ethoxycarbonylmethyl)-1-methylpyrrolidinium bromide;
    (xi) (2R,1'R,3'R) 3-(2-cyclopentyl-2-phenyl-2-hydroxyacetoxy)-1-(ethoxycarbonylmethyl)-1-methylpyrrolidinium bromide;
    (xii) (2R,1'S,3'R) 3-(2-cyclopentyl-2-phenyl-2-hydroxyacetoxy)-1-(ethoxycarbonylmethyl)-1-methylpyrrolidinium bromide;
    (xiii) (2R,1'R,3'S) 3-(2-cyclopentyl-2-phenyl-2-hydroxyacetoxy)-1-(methoxycarbonylmethyl)-1-methylpyrrolidinium bromide;
    (xiv) (2R,1'S,3'S) 3-(2-cyclopentyl-2-phenyl-2-hydroxyacetoxy)-1-(methoxycarbonylmethyl)-1-methylpyrrolidinium bromide;
    (xv) (2R,1'R,3'R) 3-(2-cyclopentyl-2-phenyl-2-hydroxyacetoxy)-1-(methoxycarbonylmethyl)-1-methylpyrrolidinium bromide; and
    (xvi) (2R,1'S,3'R) 3-(2-cyclopentyl-2-phenyl-2-hydroxyacetoxy)-1-(methoxycarbonylmethyl)-1-methylpyrrolidinium bromide.

34. The intra-oral composition according to claim 28, wherein the compound of formula (2) is (2R,3'R) 3-(2-cyclopentyl-2-phenyl-2-hydroxyacetoxy)-1-(ethoxycarbonylmethyl)-1-methylpyrrolidinium bromide or (2R,3'R) 3-(2-cyclopentyl-2-phenyl-2-hydroxyacetoxy)-1-(methoxycarbonylmethyl)-1-methylpyrrolidinium bromide.

35. A composition inhibiting acetylcholine from binding to salivary muscarinic cholinergic receptors, the composition comprising at least one compound having the formula:

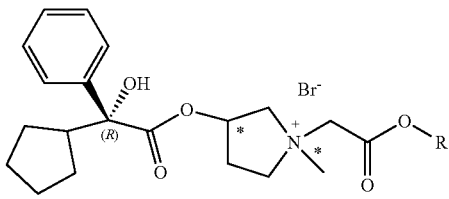

(2)

wherein R is methyl or ethyl, said compound having the R stereoisomeric configuration at the 2-position and the R, S or RS stereoisomeric configuration at the 1' and 3'-positions, or being a mixture thereof, and a pharmaceutically acceptable non-toxic carrier or excipient therefor, wherein the carrier or excipient is suitable for delivery of the composition to the salivary glands.

36. A composition for inducing dry mouth, the composition comprising an effective amount of at least one compound having the formula:

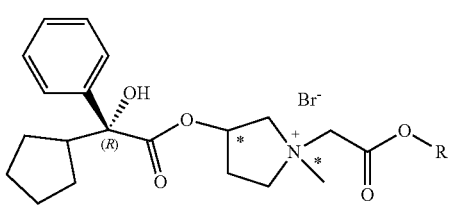

(2)

wherein R is methyl or ethyl, said compound having the R stereoisomeric configuration at the 2-position and the R, S or RS stereoisomeric configuration at the 1' and 3'-positions, or being a mixture thereof, and a pharmaceutically acceptable non-toxic carrier or excipient therefor, wherein the composition is formulated for topical administration, and wherein the induced dry mouth is sufficient to minimize or substantially reduce salivation, and wherein the carrier or excipient is suitable for delivery of the composition to the salivary glands.

37. A patch for treating sialorrhea, the patch comprising at least one compound having the formula:

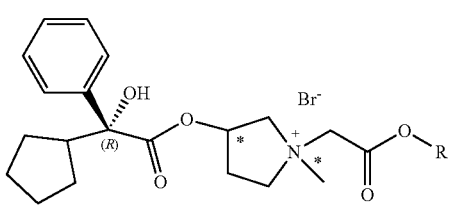

(2)

wherein R is methyl or ethyl, said compound having the R stereoisomeric configuration at the 2-position and the R, S or RS stereoisomeric configuration at the 1' and 3'-positions, or being a mixture thereof, and a pharmaceutically acceptable non-toxic carrier or excipient therefor, in an amount of compound of formula (2) of from about 1 mg to about 10 mg per adult dose, or from about 0.02 mg/kg to about 1.0 mg/kg per pediatric dose, wherein the carrier or excipient is suitable for delivery of the composition to the salivary glands.

38. An intra-oral composition, said composition comprising:

(a) at least one compound having the formula:

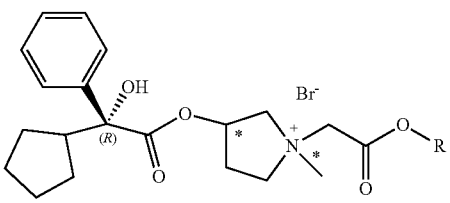

(2)

wherein R is methyl or ethyl, said compound having the R stereoisomeric configuration at the 2 position and the R, S or RS stereoisomeric configuration at the 1' and 3' positions, or being a mixture thereof; and (b) a taste masking agent; and that said intra-oral composition comprises an anti-excessive-salivation effective amount of from about 1 mg to about 10 mg per adult dose of the compound of formula (2), or from about 0.02 mg/kg to about 1.0 mg/kg per pediatric dose of the compound of formula (2); and that said intra-oral composition which is capable of dissolving in the mouth.

39. The intra-oral composition of claim 38, wherein the taste masking agent is a flavoring agent, a sweetener, a flavorless masking agent, and/or combinations thereof.

40. The intra-oral composition of claim 39, wherein the flavoring agent is a flavor oil, a flavoring aromatic, an oleo resin, a natural or synthetic extract, an essence, and/or combinations thereof.

41. The intra-oral composition of claim 40, wherein the flavoring oil is a spearmint oil, a cinnamon oil, a peppermint oil, a clove oil, a bay oil, a thyme oil, a cedar leaf oil, an oil of nutmeg, an oil of sage, an oil of bitter almonds, and/or combinations thereof.

42. The intra-oral composition of claim 40, wherein the extract is a plant extract, a leaf extract, a flower extract, a fruit extract, and/or combinations thereof.

43. The intra-oral composition of claim 40, wherein the extract is a vanilla extract, a chocolate extract, a coffee extract, a cocoa extract, a grape extract, a citrus oil extract.

44. The intra-oral composition of claim 39, wherein the essence is an apple essence, a pear essence, a peach essence, a strawberry essence, a raspberry essence, a cherry essence, a plum essence, a pineapple essence, an apricot essence, and/or combinations thereof.

45. The intra-oral composition of claim 39, wherein the flavoring agent is an aldehyde, an ester, and/or combinations thereof.

46. The intra-oral composition of claim 39, wherein the flavoring agent is a cinnamyl acetate, a cinnamaldehyde, a citral, a diethylacetal, an eugenyl formate, a p-methylanisole, and/or combinations thereof.

47. The intra-oral composition of claim 39, wherein the flavoring agent is an alpha citral, a neral, a beta citral, a decanal, an ethyl vanillin, a heliotropine, a piperonal, a vanillin, an alpha-amyl cinnamaldehyde, an aldehyde C-8, an aldehyde C-9, an aldehyde C-12, a 2-ethyl butyraldehyde, a hexenal, a trans-2 hexenal, a tolyl aldehyde, a veratraldehyde, a 2,6-dimethyl-5-heptenal, a melonal, a 2,6-dimethyloctanal, a 2-dodecenal, a quaternary ammonium base, and/or combinations thereof.

48. The intra-oral composition of claim 39, further comprising a flavor enhancer.

49. The intra-oral composition of claim 48, wherein the flavor enhancer is a tartaric acid, a citric acid, a vanillin, an alcohol, and/or combinations thereof.

50. The intra-oral composition of claim 49, wherein the alcohol is a menthol, a higher alcohol, and/or combinations thereof.

51. The intra-oral composition of claim 39, wherein the flavoring agent is present in an amount of from about 0.0001% by weight to about 5% by weight.

52. The intra-oral composition of claim 39, wherein the sweetener is a sugar and/or sugar substitutes, a cyclamate and/or salts thereof, a saccharin and/or salts thereof, an ammonium glycyrrhizinate, a aspartame, and/or combinations thereof.

53. The intra-oral composition of claim 52, wherein the sugar is a sucrose, a lactose, a glucose, sucralose, stevia, and/or combinations thereof.

54. The intra-oral composition of claim 39, wherein the sweetener is present in an amount of from about 0.001% by weight to about 70% by weight.

55. The intra-oral composition of claim 39, wherein the flavorless masking agent is a suitable coating material.

56. The intra-oral composition of claim 42, wherein the suitable coat is (i) a hydroxypropyl methylcellulose, (ii) a ethylcelluclose, (iii) a methacrylate, (iv) a polyvinylpyrrolidone, (v) a copolymer of methylacrylic acid and ethyl acrylate, and (vi) combinations thereof.

57. The intra-oral composition of claim 39, wherein the masking agent is a coat of a water-insoluble polymer.

58. The intra-oral composition of claim 39, wherein the masking agent is ethylcellulose.

* * * * *